US006700038B1

(12) United States Patent
Dasgputa et al.

(10) Patent No.: US 6,700,038 B1
(45) Date of Patent: Mar. 2, 2004

(54) PLANT EXPRESSION VECTORS BASED ON THE FLOCK HOUSE VIRUS GENOME

(75) Inventors: Ranjit K. Dasgputa, Madison, WI (US); Robert Goodman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/281,851

(22) Filed: Mar. 31, 1999

(51) Int. Cl.$^7$ .................. C12N 15/82; C12N 15/83; C12N 15/87; A01H 5/00
(52) U.S. Cl. ............. 800/278; 435/69.1; 435/69.7; 435/320.1; 435/419; 435/468; 435/471; 800/280; 800/285; 800/298; 800/317.3
(58) Field of Search ................. 435/410, 419, 435/468, 69.1, 320.1, 69.7; 536/23.72, 471; 800/278, 295, 298

(56) References Cited

FOREIGN PATENT DOCUMENTS

WO          97/20470        6/1997   ............ A10H/5/00

OTHER PUBLICATIONS

Xiong et al, Virology, vol. 171, pp. 543–554, 1989.*
Abel et al, Science, vol. 232, pp. 738–743, 1986.*
Xiong et al, Virology, vol. 192, pp. 27–32, 1993.*
Fujiwara et al, Plant Cell, vol. 5, pp. 1783–1794, 1993.*
Solovyev et al, Intervirology, vol. I 40, pp. 1–6, 1997.
Zhong et al, Proc. Natl. Acad. Sci., USA, vol. 89, pp. 11146–11150, 1992.
Selling et al, Proc. Natl. Acad. Sci., USA, vol. 87, pp. 434–438, 1990.
Day et al, "Expression of an antisense viral gene in transgenic tobacco confers resistance to the DNA virus tomato golden mosaic virus", Aug. 1991, Proc. Natl. Acad. Sci. vol. 88, pp. 6721–6725.*
Datla et al, "A bifunctional fusion between B–glucuronidase and neomycin phosphotransferase: a broad–spectrum marker ensyme for plants", 1991, Gene VI. 101, pp. 239–246.*
Dasgupta et al, "Systemic spread of an RNA insect virus in plants expressing plant viral movement protein genes", Apr. 24, 2001, PNAS vol. 98 No. 9, pp. 4910–4915.*
Giesman–Cookmeyer et al, "Tobamovirus and Dianthovirus Movement Proteins Are Functionally Homologous", 1995, Virology vol. 213, pp. 38–45.*
Morozov et al, "Complementation of a potato virus X mutant mediated by bombardment of plant tissue with cloned viral movement proteins genes", 1997, Journal of General Virology vol. 78, pp. 2077–2083.*

Beffa et al, Cholera toxin elevates pathogen resistance and induces pathogenesis related gene expression in tobacco, 1995, The Embo Journal, vol. 14 No. 23, pp. 5753–5761.*
Warkentin et al., Plant Science, 1992, vol. 87, pp. 171–177.*
Helloco–Kervarrec et al., J. Virol. Meth., 2002, vol. 102, pp. 161–166.*
Johnson, K.L., et al., "Replication of Flock House Virus RNAs from Primary Transcripts Made in Cells by RNa Polymerase II", *J. of Virology, vol. 71, No. 4, XP002149808*, 3323–3327, (Apr. 1997).
Price, B.D., et al., "Complete Replication of an animal virus and maintenance of expression vectors derived from it in *Saccharomyces cerevisiae*", *Proc. of the Nat'l Aca. of Sciences of USA, vol. 93, No. 18, XP–002149806*, 9465–9470, (Sep. 3, 1996).
Ball, L.A., et al., "Chapter 8: Nodaviruses of Insects", *The Insect Viruses*, Lois K. Miller, et al., (Eds), Plenum Press, New York, 225–267, (1998).
Dasgupta, R., "Near identity in the polymerase gene of two serologically distinct nodaviruses", *NCBI Sequence Viewer, Accession No. X77156*, 3 p., (1994).
Dasgupta, R., et al., "Systemic spread of an RNA insect virus in plants expressing plant viral movement protein genes", *Proc. Natl. Acad Sci USA 24; 98(9)*, 4910–5000, (Apr. 24, 2001).
Dasmahapatra, B., et al., "Structure of the black beetle virus genome and its functional implications", *NCBI Sequnce Viewer, Accession No. X02396 K02560*, 3 p., (1985).
Henry, D.A., "Chapter 8: Nodavriridae of Invertebrates", *Viruses of Invertebrates*, E. Kurstak, (Ed), Marcel Dekker, Inc., New York, 227–276, (1991).
Johnson, K.N., et al., "Comparisons among the large genome segments of six nodaviruses and their encoded RNA replicases", *Journal of General Virology 82*, 1855–1866, (2001).
Kaesberg, P., et al., "Structural Homology Among Four Nodaviruses as Deduced by Sequencing and X–ray Crystallography", *J. Mol. Biol. 214*, 423–435, (1990).
Valle, L. D., et al., "Sequence comparison and phylogenetic analysis of fish nodaviruses based on the coat protein gene", *Arch Virol 146*, 1125–1137, (2001).

* cited by examiner

*Primary Examiner*—Ashwin Mehta
(74) *Attorney, Agent, or Firm*—Schwegman, Lundberg, Woessner & Kluth, P.A.

(57) ABSTRACT

The invention provides insect viral vectors useful to transfer genes to plants, insects and other hosts.

49 Claims, 16 Drawing Sheets

(4 of 16 Drawing Sheet(s) Filed in Color)

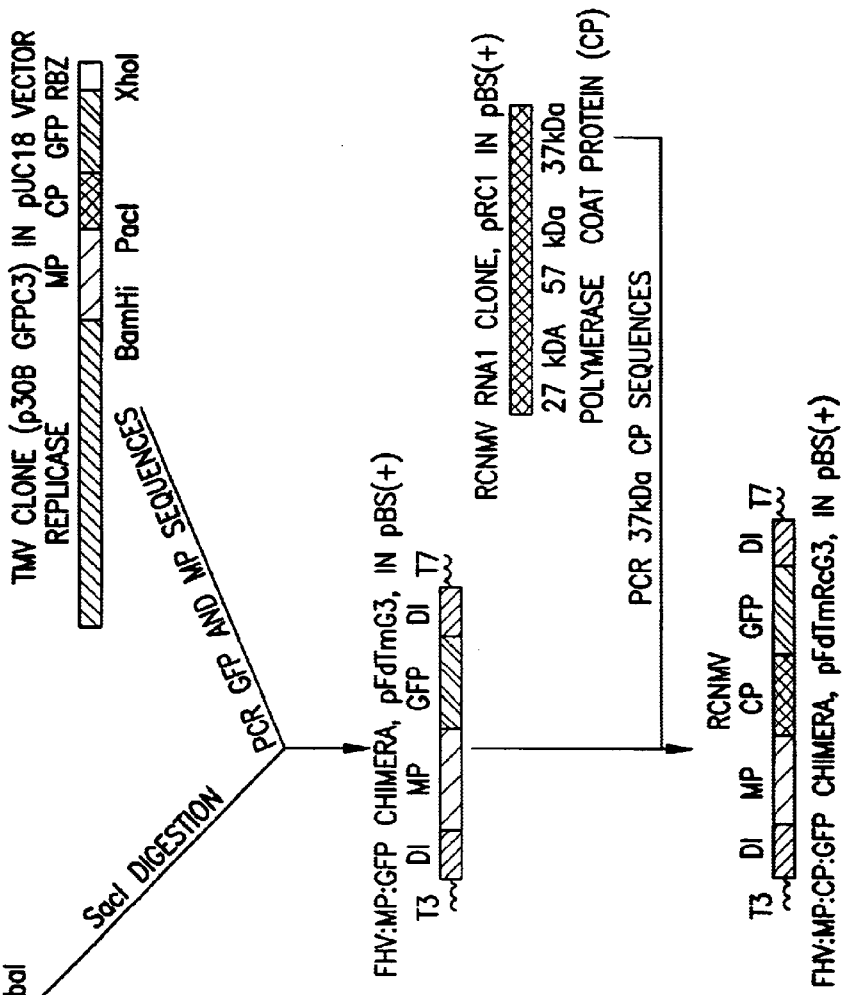

MONITORING EXPRESSION OF FHV-BASED VECTOR CONSTRUCTS ON NICOTIANA BENTHAMIANA PLANTS

| INOCULATE WITH | WILD TYPE/TRANSGENIC N. BENTHAMIANA PLANTS | DECTION PROCEDURE |
|---|---|---|
| TMV:GFP p30BGFPC3 (POSITIVE CONTROL) | | FLUORESCENCE MEASUREMENT/RT-PCR |
| FHV RNAs (POSITIVE CONTROL) | | PLAQUE ASSAY |
| FHV DI634 RNA (NEGATIVE CONTROL) | | RT-PCR/NORTHERN |
| FHV RNA-GFP (pF2G3) | | FLUORESCENCE MEASUREMENT/RT-PCR |
| FHV DI634-TMV MP (pFdTm) | | RT-PCR/NORTHERN |
| FHV DI634-TMV MP-GFP (pFdTmG3) | | FLUORESCENCE MEASUREMENT RT-PCR/NORTHERN |
| FHV DI634-TMV MP-GFP-RCNMVCP (pFdTmRcG3) | | FLUORESCENCE MEASUREMENT RT-PCR/NORTHERN |

FIG. 11

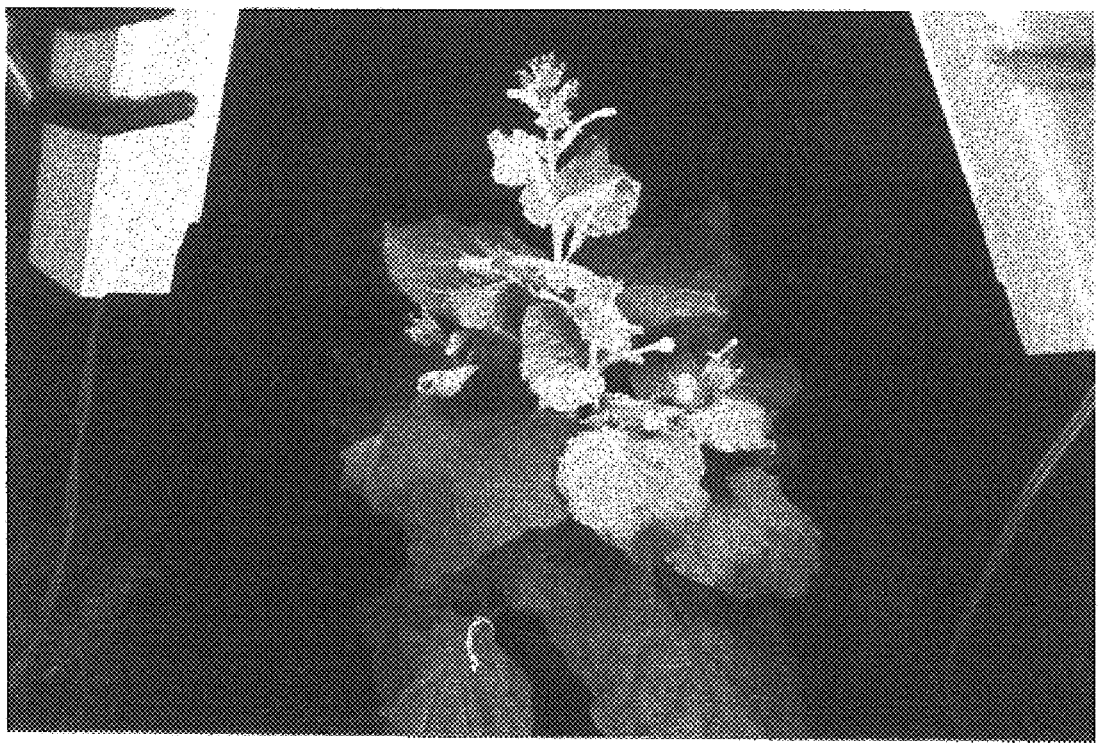
FIG. 13B

FHV YIELD IN PLANTS

| PLANT | TYPE | pfu/LEAF |
|---|---|---|
| BARLEY (HORDEUM VULGARE) | MONOCOT | $3.8 \times 10^3$ |
| RICE | MONOCOT | $4.2 \times 10^5$ |
| SWEET CORN | MONOCOT | $6.2 \times 10^6$ |
| ALFALFA | DICOT | $5.3 \times 10^4$ |
| BRASSICA | DICOT | $2.8 \times 10^5$ |
| CUCUMBER | DICOT | $3.0 \times 10^7$ |
| COWPEA (VIGNA SINESIS) | DICOT | $4.2 \times 10^7$ |
| CHENOPODIUM HYBRIDUM | DICOT | $3.4 \times 10^5$ |
| TOBACCO (N. TABACUM) | DICOT | $8.2 \times 10^4$ |
| N. BENTHAMIANA (WT) | DICOT | $1.2 \times 10^5$ |
| N. BENTHAMIANA (MP)* | DICOT | $1.1 \times 10^7$ |

PFU=PLAQUE FORMING AMOUNT=322 VIRUS PARTICLES

*TRANSGENIC PLANT EXPRESSING TMV MP

FIG. 17

SEQUENCE LISTING

<160> NUMBER OF SEQ ID NOS: 10

<210> SEQ ID NO 1
<211> LENGTH: 16
<212> TYPE: DNA
<213> ORGANISM: Flock house virus

<400> SEQUENCE: 1
accttagtct gttgac                                                      16

<210> SEQ ID NO 2
<211> LENGTH: 15
<212> TYPE: DNA
<213> ORGANISM: Flock house virus

<400> SEQUENCE: 2
gtaaacaatt ccaag                                                       15

<210> SEQ ID NO 3
<211> LENGTH: 44
<212> TYPE: RNA
<213> ORGANISM: Flock house virus

<400> SEQUENCE: 3
uggcggcgcu aaccagauua agucaaccug guuggcguu ucuc                        44

<210> SEQ ID NO 4
<211> LENGTH: 44
<212> TYPE: RNA
<213> ORGANISM: Black beetle virus

<400> SEQUENCE: 4 uggggggcgcu gaccaggcuu agucaaccug guuuagcguu ucuc                      44

<210> SEQ ID NO 5
<211> LENGTH: 44
<212> TYPE: RNA
<213> ORGANISM: Boolarra virus

<400> SEQUENCE: 5
cguuggcuuc gccggauccc aacacggauc cuggcaaggu auac                       44

<210> SEQ ID NO 6
<211> LENGTH: 45
<212> TYPE: RNA
<213> ORGANISM: Nodamura virus

<400> SEQUENCE: 6
ccuuugcuuc gccggauuuu uccaccgauc ccggcaaagg uauuc                      45

<210> SEQ ID NO 7
<211> LENGTH: 27
<212> TYPE: DNA
<213> ORGANISM: Artificial Sequence
<220> FEATURE:
<223> OTHER INFORMATION: A primer -continued

```
<400> SEQUENCE: 7
gcatgcatag catatatggc tgcaaag                                               27

<210> SEQ ID NO 8
<211> LENGTH: 24
<212> TYPE: DNA
<213> ORGANISM: Artificial Sequence
<220> FEATURE:
<223> OTHER INFORMATION: A primer

<400> SEQUENCE: 8
gtacatgcat tgtagagctc atcc                                                  24

<210> SEQ ID NO 9
<211> LENGTH: 29
<212> TYPE: DNA
<213> ORGANISM: Artificial Sequence
<220> FEATURE:
<223> OTHER INFORMATION: A primer

<400> SEQUENCE: 9
cggaattcga gctcagatgg ctctagttg                                             29

<210> SEQ ID NO 10
<211> LENGTH: 17
<212> TYPE: DNA
<213> ORGANISM: Artificial Sequence
<220> FEATURE:
<223> OTHER INFORMATION: A primer

<400> SEQUENCE: 10
cttgactacc cctcgag                                                          17
```

PLANT EXPRESSION VECTORS BASED ON THE FLOCK HOUSE VIRUS GENOME

STATEMENT OF GOVERNMENT RIGHTS

This invention was made with a grant from the Government of the United States of America (Grant No. CR822902 from the Environmental Protection Agency, Grant Nos. 58-3148-6-029 and 94-34190-1204 from the United States Department of Agriculture, and Award No. 94-39210-0559 from AGRICCREE). The Government may have certain rights in the invention.

BACKGROUND OF THE INVENTION

Synthesis of useful compounds in plants, e.g., therapeutic agents, chemical feedstocks, cosmetics and other consumer goods, and genetic engineering for crop improvement, for example, genetically engineered pathogen-resistant plants, are two areas of plant biotechnology that are of increasing economic importance and research interest around the globe (Miele, 1997; Franken et al., 1997; Beachy, 1997; Ma et al., 1996; Estruch et al., 1997; Palmgren, 1997). In addition, the availability of plant genomic and EST libraries is changing the potential for commercial plant biotechnology (Briggs et al., 1997; McKusick, 1997; and Evans. et al., 1997). In particular, because many plant traits, such as yield, harvest index, heterosis, and environmental stress tolerance, are regulated by the concerted action of several genes, access to gene sequence tags and genomic libraries provides a means to identify, or a ready source for, genes that are of commercial interest.

Vectors based on several plant viruses, for example, tobacco mosaic virus (TMV), Cowpea Mosaic Virus (CpMV), Bromoviruses (e.g., BMV) and Potyviruses (Yusibov et al., 1997; Reimann-Phillip et al., 1993; Porta et al., 1996; Johnson et al., 1997; Kollar et al., 1993; Pruss et al., 1997), are being developed to introduce selected genes into plants for the synthesis of useful compounds. Virus-based vectors offer several distinctive advantages for gene transfer that complement Agrobacterium-mediated transformation and particle bombardment methods. Viral vectors are easily manipulated; they can be transferred by simple inoculation and they permit high levels of expression in transfected plants. However, the existing plant virus-based vector systems have their limitations. They can cause disease in their plant hosts, ranging from minor to catastrophic. Also, they naturally spread in nature, from one plant to another in the field, and in some cases they can be spread through pollen or seed to the next generation. Moreover, many of these viruses have narrow host ranges and have limited utility due to variable expression of foreign genes.

Nodaviruses are small, non-enveloped icosahedral viruses of insect origin. Mosquitoes (*Culex tritaeniorhynchus, Aedesa egypti, Culex tarsalis, Aedes albopictus* and *Toxorhynchites amboinesis*), larvae of the Indian meal moth and the black carpet beetle (*Plodia interpunctella*: Lepidoptera and *Attagenus piceus*: Coleoptera), larvae of the wax moth (*Galleria mellonella*: Lepidoptera) and honey bee (*Apis mellifera*) are some of the insect hosts known to be infected by nodaviruses and in which virus infection causes paralysis and death (Tesh, 1980; Bailey and Scott, 1972). Exemplary nodaviruses include Black beetle virus (BBV), Flock House virus (FHV), Boolarra virus (BOV) and Nodamura virus (NOV). These viruses are the only known messenger sense, bipartite genome RNA viruses of higher or lower animals (for a review, see Hendry, 1991). Bipartite genome plant viruses are known, but their genome parts are encapsidated in separate virions (Bruening, 1977).

The natural hosts of Nodaviruses are insects, however, Nodaviruses can multiply in animals (for example, NOV can infect mice and possibly pigs, see Bailey and Scott, 1972; Scherer and Hurlbut, 1967; Scherer et al., 1968), and recently have been found in marine fish (Mori et al., 1992; Nishizawa et al., 1995; Frerichs et al., 1996), although FHV does not multiply at all in higher animal cells. In addition, FHV readily multiplies in plants without causing disease symptoms (Selling et al., 1990). FHV can be introduced to plants by mrechanically rubbing the leaves or may be introduced by spraying the leaves with a solution containing the virus. However, FHV moves poorly or not at all from the site of infection.

Thus, what is needed is a vector to systemically or locally transmit a desired or preselected nucleic acid segment or sequence to plants without causing disease to those plants.

SUMMARY OF THE INVENTION

The present invention provides a recombinant viral nucleic acid-based gene transfer vector useful to transmit genes to plants and animals, e.g., insects. Preferably, the vector is derived from a virus having a bipartite genome which comprises single strand linear RNA, e.g., Nodavirus (Hendry, 1991), Dianthovirus, Tobravirus (Matthews, 1991) and the like. Thus, the invention provides a biologically active gene transfer vector, comprising linked nucleic acid sequences. The linked nucleic acid sequences include a nucleic acid sequence derived from the 5' end of a viral nucleic acid, e.g., the 5' end of Nodavirus RNA-1 or Nodavirus RNA-2; a nucleic acid sequence comprising at least one nucleic acid segment of interest; and a nucleic acid sequence derived from the 3' end of a viral nucleic acid, e.g., the 3' end of Nodavirus RNA-1 or Nodavirus RNA-2. The nucleic acid sequence comprising the nucleic acid segment of interest preferably encodes a plant virus movement protein, a plant virus coat protein (e.g., a native coat protein or a modified coat protein having different properties than the native coat protein), a growth hormone, a toxin, e.g., a sublethal toxin such as an auxin or a Photorhabdus toxin, a cytokine, disease resistance, pest resistance, male sterility, antigenic sites on the surface of a virus useful for vaccine production, or pesticide resistance, and/or comprising a synthetic gene, targeted antisense RNA sequences/enzymes to modify plant properties, a marker gene or a selectable marker, or any combination thereof. Preferably, a nucleic acid segment comprises sequences modified for enhanced expression in plants. The nucleic acid segment(s) are preferably linked so as to result in a fusion polypeptide. Alternatively, nucleic acid sequences encoding proteolytic sites may be introduced between each nucleic acid segment. Optionally, each nucleic acid segment may be operably linked to a transcription control unit, e.g., a promoter. A vector of the invention may be combined with other animal virus-based vectors, plant virus-based vectors or other insect virus-based vectors, for example, a tobacco mosaic virus-based vector (Beachy, 1997), a baculovirus-based vector (Schneemann et al., 1993) or a vaccinia virus-based vector (Ball, 1992).

A preferred vector of the invention comprises Nodavirus nucleic acid at the 5' and 3' ends of the vector and encodes a plant virus movement protein (MP). MP assists in the translocation of a virus or viral nucleoprotein (genetic material plus "carrier protein") from plant cell to plant cell. Thus, the expression of a MP in a plant cell having a vector of the invention leads to the transmission of vector sequences to surrounding plant cells, which results in a local or transient transmission and expression of those sequences.

Thus, where transient or localized expression is desirable and sufficient (as in high throughput screening/genomics), the transmission of a vector of the invention can dramatically reduce the time to screen for expression compared to a transgenic approach. In addition, since Nodaviruses, Dianthoviruses and Tobraviruses can be transmitted by simple mechanical rubbing of leaves, vectors based on these viruses may be used on existing varieties of plants without the need to prepare transgenic versions. In particular, the invention provides an approach to crop improvement which avoids the time-consuming and expensive methods needed to prepare transgenic crops and avoids the potential for contamination of seed banks and germplasm collections with foreign genes, which is associated with transgenic approaches.

The invention further provides a method to introduce a preselected nucleic acid sequence to a host cell. The method comprises contacting a host cell with a vector of the invention in an amount effective to express the preselected nucleic acid sequence without producing infectious virus particles. If the host is an organism, the absence of infectious virus completely eliminates the threat for any unexpected and undesirable consequences for the host, e.g., insects or human beings. Preferably, for plant hosts, the contact includes mechanical rubbing, e.g., of the leaves.

The invention also provides compositions useful to transfer genes to host cells. One embodiment of a composition of the invention includes (a) an amount of nucleic acid encoding a viral polymerase (replicase), such as Nodavirus RNA-1; and (b) an amount of recombinant nucleic acid. The recombinant nucleic acid comprises a nucleic acid sequence derived from the 5' end of a viral nucleic acid, e.g., the 5' end of Nodavirus RNA-2; nucleic acid sequence comprising at least one nucleic acid segment of interest; and a nucleic acid sequence derived from the 3' end of a viral nucleic acid, e.g., the 3' end of Nodavirus RNA-2. The presence of nucleic acid encoding a viral replicase, e.g., RNA-1 of Nodavirus, in a composition of the invention permits amplification of nucleic acid molecules which are cotransferred to host cells with the nucleic acid encoding the replicase. Alternatively, the replicase may be encoded by the host cell. A preferred nucleic acid sequence encoding a replicase includes FHV RNA-1. RNA molecules can be prepared in vitro, e.g., using T7, T3 or SP6 polymerase, or by isolating RNA from virions or from cultured cells, e.g., rodent, Drosophilia or insect cells, that have been transfected or contacted with RNA or DNA molecules, or compositions, of the invention.

If systemic transfer of a gene of interest is desired, one of the nucleic acid sequences in a composition of the invention preferably encodes la CP, and optionally also encodes a MP, so that the vector is transmitted to the vascular tissue (the phloem). The expression of CP and MP can permit the synthesis of desired compounds in high yields, and may result in conferring disease resistance to all plant tissues. As described hereinbelow, a FHV-based vector for systemic infection of plants may be prepared which includes the 30 kDa movement protein of Tobacco Mosaic Virus (TMV MP; Deom et al., 1992) and the coat protein of a Red Clover Necrotic Mosaic Virus (RCNMV; Xiong et al., 1993). To monitor the movement of the vector through the plant, a marker gene may be introduced into the vector, e.g., a gene encoding green fluorescent protein (GFP, Epel et al., 1996; and Casper et al., 1996). GFP is a protein of 238 amino acid residues originally isolated from the jelly fish *Aequorea victoria* (*Av*). It absorbs blue light with maximal absorption at 395 nm and emits green light with peak emission at 590 nm. When GFP is expressed in either prokaryotic or eukaryotic cells, it is capable of producing a strong green fluorescence when excited by the blue light and this fluorescence requires no additional gene products from its host.

Thus, the vectors and compositions of the invention can be used to synthesize desired pharmacological compounds or other agents, e.g., agents encoding insect resistance, and for high throughput screening of uncharacterized genetic material, e.g., uncharacterized genetic material from a pesticide-resistant plant or insect nucleic acid encoding a useful trait. For example, uncharacterized genetic material from a pest-resistant plant is introduced into a vector of the invention, RNA is then expressed therefrom and a composition of the invention is prepared. Plants that are susceptible to the pest are exposed to the composition, preferably by spraying, and are then exposed to pest infestation. Leaves that exhibit signs of resistance are indicative that the introduced genetic material may encode pest resistance.

Thus, the invention also provides a quick assay system for developmental genes, regulatory genes, and genes for drug resistance and toxicity in insects and humans.

For applications in which a recombinant protein is to be expressed and then isolated from the host plant, e.g., a pharmaceutical compound, the composition of the invention is preferably applied to the plant by rubbing or spraying. For example, the contacted area of the plant may be such that only foliage of the plant is exposed to the composition, for example, plants such as tubers whose foliage has no commercial value. Once the protein is expressed in the plant, the recombinant protein(s) can be isolated and/or purified from the plant or its tissues.

Also provided is a method of expressing a preselected nucleic acid molecule in a host cell or host. The method comprises contacting a host cell or host with an amount of a composition of the invention. Preferred compositions include recombinant virus, isolated virion RNAs, in vitro-prepared RNA transcripts, or any combination thereof. Then the expression of the gene of interest is detected or determined. Hence, the invention further provides a transgenic host, the genome of which is augmented with the vector of the invention.

Preferred plant hosts for the gene transfer vectors and compositions of the invention include transgenic and non-transgenic monocots and dicots, e.g., Brassica, sweet corn, cucumber, barley, chenopodium, e.g., *Chenopodium hybridum*, cowpea, tobacco and *Nicotiana benthamiana* and the like. Preferably, the plant host is susceptible to Nodavirus infection.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 10: Construction of a Nodavirus DI-based vector encoding TMV MP, Red Clover Necrotic Mosaic Virus coat protein (RCNMV CP) and GFP. RCNMV coat protein sequence is amplified from RCNMV cDNA clone pRC1 and inserted in between MP and GFP sequences of pFdTmG3 as described above to create pFdTmRcG3. T3=T3 promoter; T7=T7 promoter; RBZ=ribozyme.

FIG. 11: Monitoring expression of FHV-based vector constructs on *Nicotiana benthamiana* plants. Leaves are inoculated by rubbing the leaves with RNA transcripts made in vitro using T3 or T7 RNA polymerase. All plants are co-inoculated with FHV RNA-1 as a source of FHV replicase.

FIG. 13B: Photograph of *N. benthamiana* plants expressing GFP. Conditions were the same as in FIG. 13A except that the photograph was taken using a Minolta MaMaxxum 7000i camera and 1000 ASA Kodak Ectachrome film. The film was exposed for 4 seconds.

FIG. 17: FHV yield in plants. Yields are determined by plaque assay of leaf homogenates on a monolayer of Drosophila cells. Yields are expressed in plaque forming units (pfu) per mg leaf tissue (100–500 mg). Note a 100-fold increase in transgenic *N. benthamiana* plants compared to non-transformed (wild-type) plants.

DETAILED DESCRIPTION OF THE INVENTION

I. Nodavirus Replication and Transmission
A. Genome Organization of Nodaviruses

Figure 1:
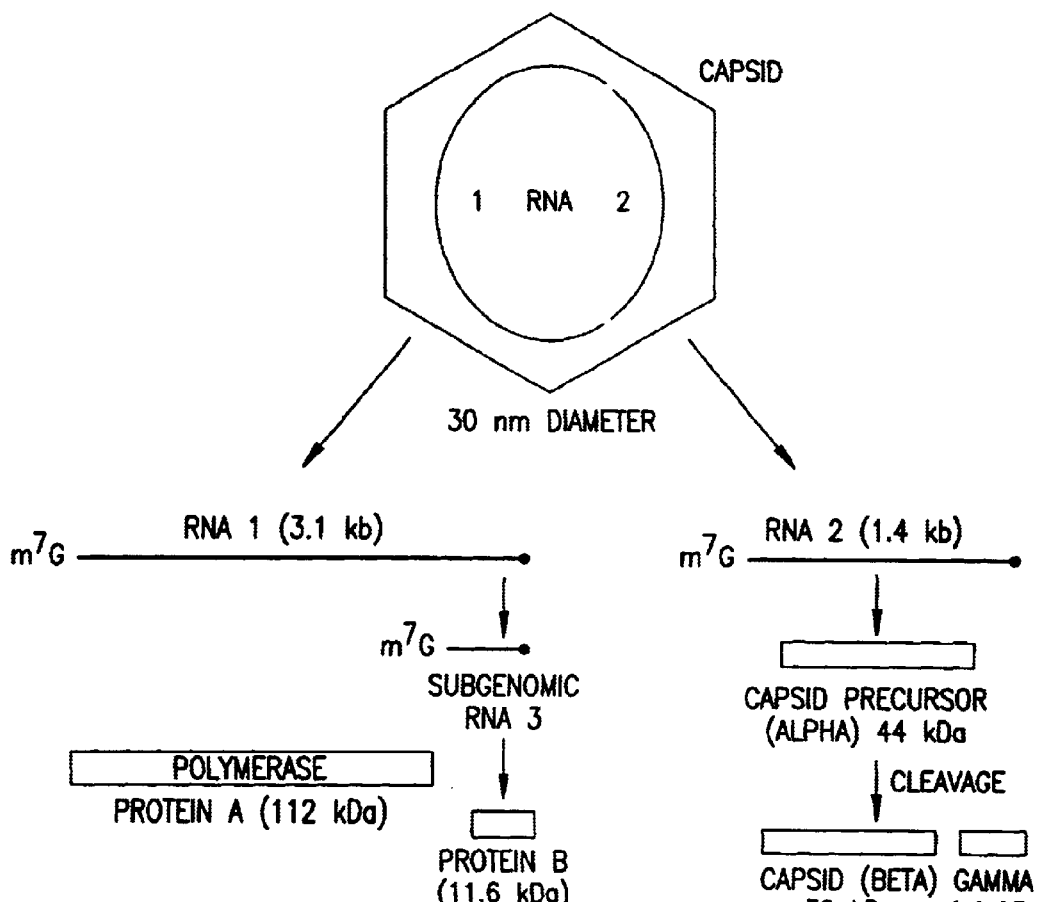
FIG. 1: Genomic organization of Flock House virus (FHV). FHV is a small icosahedral virus of 30 nm diameter with a bipartite genome. RNA-1 is capped, is about 3.1 kb in length and encodes a replicase of about 112 kDa. RNA-2 is capped, is about 1.4 kb in length and encodes a 44 kDa precursor of the coat/capsid protein. RNA-3 is also capped, about 0.39 kb in length and encodes a 11.6 kDa protein. Solid circles at the 3'-termini indicate that these ends are masked or blocked. Both RNA-1 and RNA-2 are encapsidated in the same virion.

The genome strategy of a representative Nodavirus, FHV, is shown in FIG. 1. RNA-1 and RNA-2 are sense RNAs that are encapsidated within a single virion. FHV RNA-1 (3106 bases) codes for a protein called A (112 kDa) which is responsible for the polymerase (replicase) activity. FHV RNA-2 (1400 bases) directs the synthesis of a virion capsid precursor termed alpha (44 kDa), which is processed into the mature coat protein (referred to as beta; 39 kDa) and a small 4.4 kDa protein, termed gamma. Cells infected with FHV produce an additional messenger, RNA-3 (389 bases), coding for a protein called B (11.6 kDa). RNA-3 is a subgenomic messenger RNA contained at the 3'-end of RNA-1 which is not encapsidated into virions. Protein B is involved in polymerase function. All Nodaviral RNAs are capped (m7GpppGp) at their 5'-ends and, unlike any other known RNA viruses, their 3'-termini are masked or blocked as evidenced by resistance to modification even under denaturing conditions (Dasgupta et al., 1984).

cDNA clones of both genomic RNAs are available and the in vitro RNA transcripts made from these clones are infectious and produce authentic progeny virions (Dasmahapatra et al., 1986).

B. Persistent Infection and Generation of DI RNAs

In vitro, Nodaviruses grow vigorously in *Drosophila melanogaster* cells (Friesen and Rueckert, 1981) and can be quantitatively assayed by plaque formation (Selling and Rueckert, 1984). When *Drosophila melanogaster* cells are infected with FHV at low or high multiplicity of infection (m.o.i.), e.g., 0.1–10, the virus causes extensive cytopathic effect and cell death within 3 days. However, about 1% of infected cells survive in each round of the infection cycle. These cells are resistant to superinfection by FHV and other related nodaviruses like BBV (Longworth and Archibald, 1975) and BOV (Reinganum et al., 1985). These infected cells are a source of virus that can lyse fresh cells with similar efficiency. These cells are, therefore, persistently infected in a non-lytic fashion.

Viral RNAs from ten of these persistently infected cell lines were labeled with $^3$H-uridine in the presence of actinomycin D and analyzed on agarose gels. The autoradiogram showed the presence of small RNAs in addition to the genomic RNAs in at least four out of ten lines (Selling, 1986). Some of these smaller RNAs were found in virions purified from persistently infected cells indicating that these smaller RNAs contain signals for replication and packaging. Transfection of fresh Drosophila cells with these RNAs plus virion RNAs caused a thousand-fold inhibition in plaque formation compared to the wild-type FHV. This suggested that these RNAs compete and interfere with the replication of genomic RNAs and are probably better templates for replication and encapsidation. These RNAs are referred to as defective interfering (DI) RNA molecules.

C. Structure of DI RNAs

Figure 2:
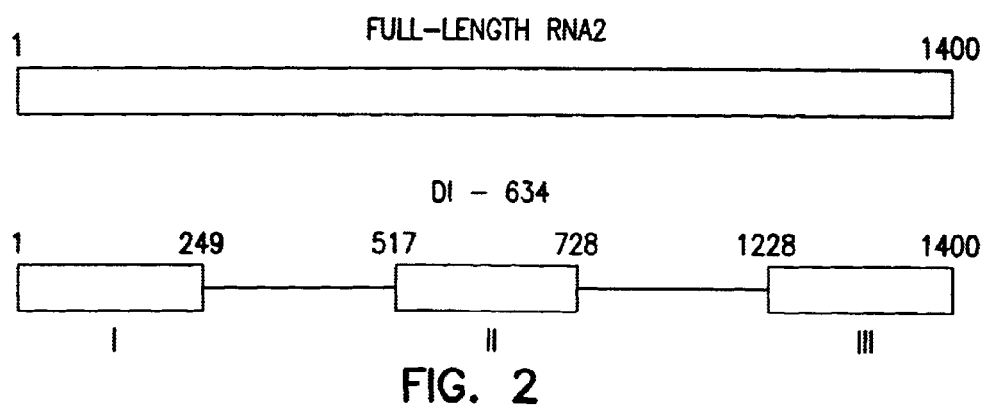
FIG. 2: Structure of FHV RNA-2 and defective interfering RNA DI-634. DI-634 is a 634 b spontaneous deletion product of RNA-2 that is efficiently replicated and packaged into virions. Segments labeled I, II, III correspond to sequences from the 5'-end, middle and 3'-ends of FHV RNA-2; thin lines represent areas deleted from RNA-2.

Enzymatic sequencing (Dasgupta et al., 1980) of DI RNAs showed that they retain sequences identical to the 3'- and 5'-ends of virion RNAs. Oligonucleotide primers corresponding to the ends of FHV RNA-1 (Dasmahapatra et al., 1985) and RNA-2 sequences (Dasgupta and Sgro, 1989) were used to make cDNA clones in pUC13 and pBS+ vectors. These cDNAs were then sequenced by the dideoxy nucleotide chain termination method using Sequenase (United States Biochemicals, Kraft et al., 1988). Seven DI RNA molecules were sequenced. Six of them were derived from genomic RNA-2 and one of them was derived from genomic RNA-1. The DI RNAs derived from RNA-2 were divided into three groups according to their structures: the simplest form of DI (DI-634), shown in FIG. 2, resulted from two major deletions in RNA-2; it retained the first 249 bases from the 5'-end, the middle (bases 517–728) and the 3'-end of RNA-2 (bases 1228–1400). There were no rearrangements of the sequences.

Another type of RNA-2 derived DI RNA sequences had a more complex structure. They retained the first 15 or 41 bases from the 5'-end of genomic RNAs which was followed by bases 75–249 and bases 517–728 derived from the middle of genomic RNA-2. The 3'-half of these DI molecules included sequence rearrangements from the 5'- and 3'-end of RNA-2. The 48 bases at the 3' end (1353–1400) were co-linear with genomic RNA-2.

Yet another form of RNA-2-derived DI retained a stretch of 249 bases from the 5'-end, and the rest of the structure included the rearrangement mentioned above.

The DI RNA derived from RNA-1 retained three parts from genomic RNA: the two ends and the middle. Interestingly, in spite of variations in the structure, all these DI RNAs were of similar length; approximately half as long as their corresponding genomic RNAs. For example, DIs derived from genomic RNA-2 were 630–680 bases long and the one DI derived from RNA-1 was 1395 bases long (genomic RNA-1 and RNA-2 are 3106 and 1400 bases, respectively).

Figure 3A:
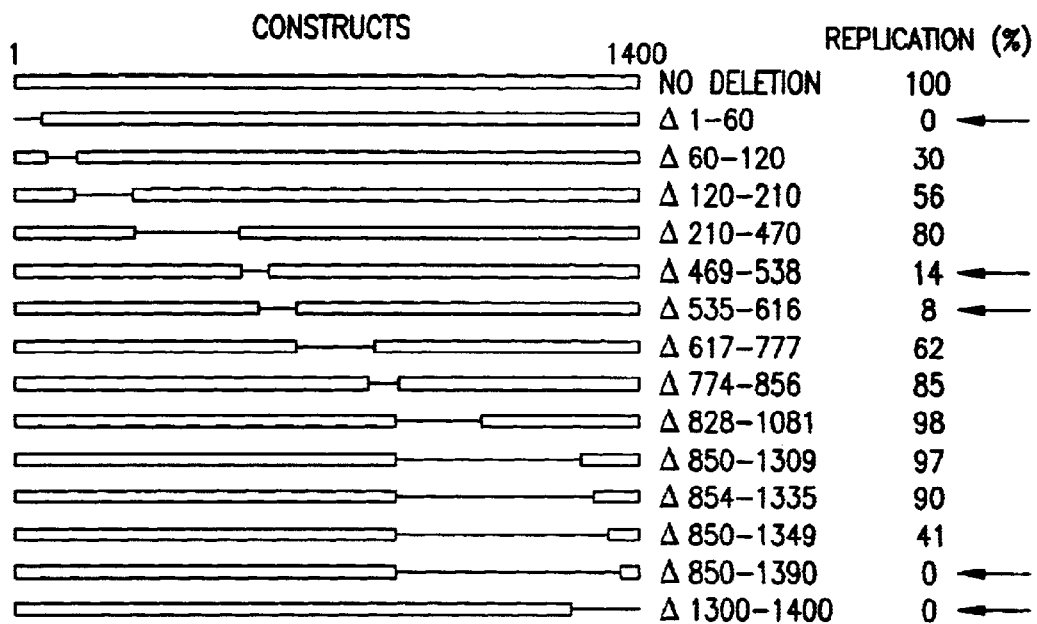
FIG. 3: Cis-acting sequences required for FHV RNA-2 replication. (A) Solid bars indicate full length cDNA clone of FHV RNA-2 or sequences of the cDNA present in deletion mutants. Thin lines indicate deleted (Δ) bases, which are indicated to the right of each construct. The replication efficiencies of deleted mutants relative to the full length clone (100%) have been measured as described by Zhong et al. (1992). Mutants with very poor replication efficiencies are indicated by arrows. (B) The solid blocks show three segments essential for FHV RNA-2 replication.
Figure 3B:
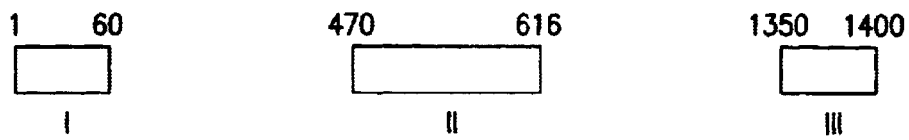

D. Signals for Replication and Encapsidation of FHV RNA-2 cDNA clones of FHV RNA-2 as well as the DI RNAs, were modified through a series of deletions and in vitro mutagenesis, and assayed for their replication and encapsidation activities. FIG. 3 is a schematic diagram showing the deletion mutants constructed from the cDNA clone of RNA-2. Transcripts derived from these mutants were used to transfect Drosophila cells and RNA synthesized after 12 hours was measured (Zhong et al., 1992). A stretch of 60 bases from the 5'-end, an internal region of 147 bases (bases 470–616), and the last 51 bases at the 3'-end (1350–1400) were found to be important for efficient replication of FHV RNA-2 (panel B; segments I, II and III, respectively). Replication of RNA-2 in vivo was very poor (shown by arrows in FIG. 3A) when these regions were deleted.

Figure 4:
FIG. 4: Computer predicted stem-loop structures (SEQ ID NOs:3–6) of putative encapsidation sequences in RNA-2s of Nodaviruses. Total length of RNA-2s of FHV, BBV, BOV and NOV are 1400, 1399, 1305 and 1355 bases, respectively (Dasgupta and Sgro, 1989).

Similar studies on encapsidation signals using DI RNA (DI-634, shown in FIG. 2) showed that a 32-base region of RNA-2 (bases 186–217) is required for efficient packaging into virions. Deletion of this region completely eliminated the packaging of DI RNA into virions but had no effect on replication. The formation of a stem-loop structure, shown in FIG. 4, has been predicted for this sequence, which is preserved in all the Nodaviral RNA-2s (Zhong et al., 1992). Similar stem-loop structures were also found to be used as packaging signals in bacteriophages Qβ and R17, the L-A viruses of the yeast and in Coronaviruses.

E. Propagation of FHV in Plants

Propagation of a virus in a host plant involves viral movement/replication in a diverse array of tissues. The virus enters a wounded cell after infection and synthesizes its own proteins. One of the nonstructural virus-encoded proteins, the movement protein (MP), allows an infectious nucleoprotein to move from cell to cell until infection reaches the vascular tissues.

During the second step, known as vascular or long distance movement, the entire plant becomes infected. To achieve this, infectious nucleoprotein must enter, move within, and leave the vascular tissues. Studies show that MP is required for cell-to-cell movement but MP alone is not enough to cause systemic infection. In most plant viruses, coat protein (CP) and host factors are necessary for long distance movement (for a review, see Seron et al., 1996; Deom et al., 1992).

Figure 5:
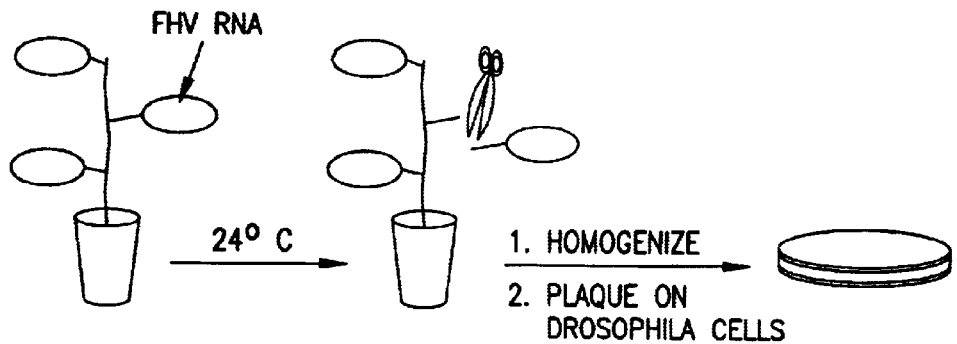
FIG. 5: Schematic diagram showing the procedure for detection of FHV synthesis in plants. Single leaves of a number of plant species were inoculated with FHV RNA as described by Selling et al. (1990). FHV infectivity, as detected by plaque assay, was found in most homogenates derived from inoculated leaves of barley, chenopodium, cowpea and *Nicotiana benthamiana*.
Figure 6:
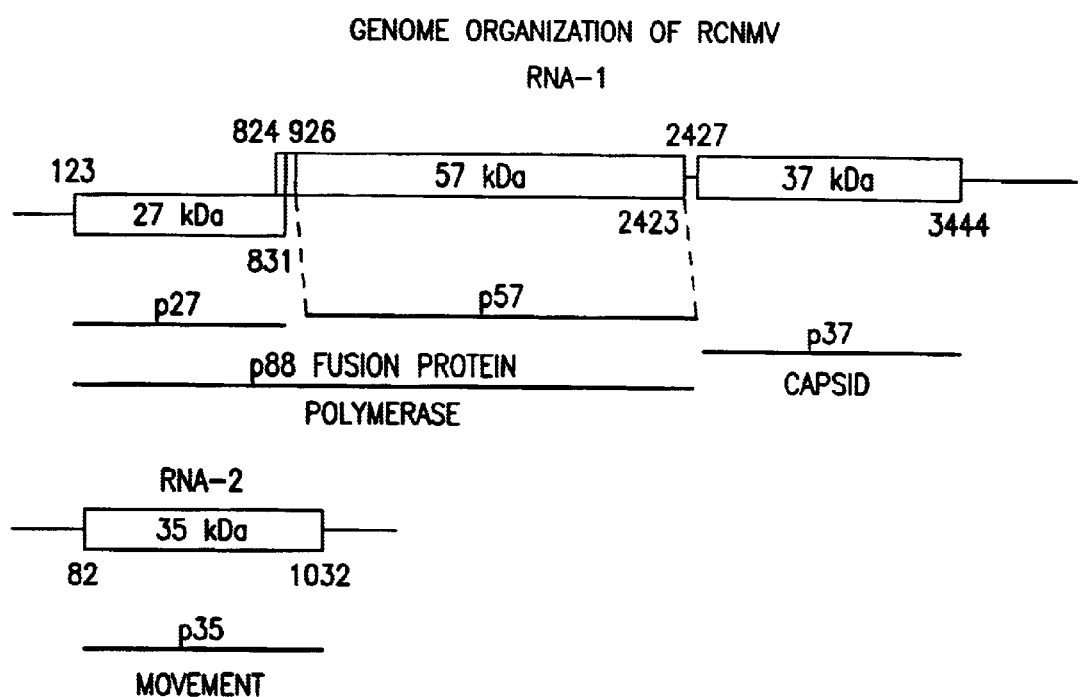
FIG. 6: Genome organization of RCNMV. RNA-1 and RNA-2 are depicted as solid lines with ORFs identified as open boxes. Numbers above or below ORFs identify the positions of ORF initiation and termination codons. The ribosomal frameshifting region in the RNA-1 is marked as a hatched box. Predicted and observed protein products are represented by black boxes. Known functions of RCNMV proteins (Matthews, 1991) are described below each protein.

To determine whether FHV replicates in a plant, the plant is inoculated with FHV RNA. Newly synthesized virions have been detected in whole plants of barley (*Hordeum vulgare*), cowpea (*Vigna sinensis*), chenopodium (*Chenopodium hybridum*), Nicotiana benthamiana (Selling, 1990), rice, alfalfa, sweet corn, brassica and cucumber (FIG. 17), and in protoplasts derived from barley and tobacco leaves (FIG. 5 and Table 1) which were exposed to FHV RNA.

TABLE 1

Virion production after virus exposure[†]

| Species | Proportion of homogenates producing plaques |
|---|---|
| Barley (*H. vulgare*) | 6/7 |
| *Chenopodium hybridum* | 6/6 |
| Cowpea (*V. sinensis*) | 7/7 |
| *Nicotiana benthamiana* | 30/30 |
| Tobacco (*N. tabacum*) | 1/8 |

[†]from Selling, 1990

In barley protoplasts, the yield of virus was 130 pfu per protoplast which represents a minimum estimate of about 3% of protoplasts that synthesize virions. Virions produced in plants contained newly synthesized RNA as well as newly synthesized capsid protein. Time course experiments showed that synthesis of FHV in barley protoplasts was quite comparable to that found in FHV's natural insect cell line host (*Drosophila melanogaster*) under comparable conditions of transfection (Selling et al., 1990). Approximately 1.4 mg of FHV was produced from 1 g of barley protoplasts which demonstrated a very high level of expression.

In two inoculated barley leaves, FHV yields were 180 and 3800 pfu (based on a standard FHV plaque assay on Drosophila cells) on a per-leaf basis. A maximum average yield of $3.4\times10^5$, $4.2\times10^5$ and $1.2\times10^5$ pfu per leaf was observed with FHV infected chenopodium, cowpea and *N. benthamiana*, respectively (FIG. 17).

In *N. benthamiana*, virions resulting from inoculation with FHV RNA were detected not only in inoculated leaves but also in other leaves of inoculated plants suggesting that virions could move in this plant species. However, in *N. benthamiana*, the movement was restricted to three leaves above and below the inoculated leaves. Moreover, there was a decrease in infectivity with time. This could be due to instability of virions in plants and/or spread of virions away from the site of inoculation. These results showed that the intracellular environment in plants is suitable for synthesis of a virus normally indigenous only to insects, although viral coded proteins necessary for cell to cell movement in plants are probably not coded by FHV.

II. Vectors of the Invention

A. Viral Sequences

The vectors of the invention comprise viral sequences necessary for the transmission of those sequences to cells, as well as sequences of interest which are linked to the viral sequences. Thus, the vectors include non-coding sequences which are necessary in cis, i.e., the 5' and 3' ends of Nodavirus, Tobravirus or Dianthavirus nucleic acid, and trans-acting sequences necessary for transmission of the vector to other cells, i.e., sequences coding for viral MP and/or CP. Dianthoviruses include carnation ringspot virus, red clover necrotic mosaic, sweet clover necrotic mosaic virus, and furcraea necrotic streak virus. Tobraviruses include pea early browning virus, pepper ring spot virus, tobacco rattle virus, and harts tongue fern virus. For amplification of vector sequences within a cell, a viral replicase may be employed. The replicase may be encoded by the host cell genome, by a nucleic acid sequence introduced into the host cell prior to, concurrent with or subsequent to the introduction of the vector, or encoded by the vector.

The vector of the invention may encode any viral MP including, but not limited to, the movement protein of Commelina yellow mottle virus (CoMYV), CaMV, sugarcane bacilliform virus (ScBV), rice tungro bacilliform virus (RTBV), carnation etched ring virus (CERV), figwort mosaic virus (FMV), soybean chlorotic mottle virus (SoyCMV), surin-hemp mosaic virus (Deom et al., 1997), tobacco necrosis virus (Molnar et al., 1997), tobacco mosaic virus (Slovyev et al., 1996), geminivirus (Sung et al., 1995), potexvirus, hordevirus and beet yellows virus (Agranovsky et al., 1998), alfalfa mosaic virus (van der Vossen et al., 1995), peanut chlorotic streak virus (Ducasse et al., 1995), artichoke mottle crinkle virus (Tavassa et al., 1994), barley stripe mosaic virus (Weiland et al., 1994), cowpea mosaic virus (Wellink et al., 1993), beet yellows mosaic virus (Karasev et al., 1992), and turnip crinkle virus (Hacker et al., 1992).

For systemic and/or local infection of a plant, the vector of the invention preferably encodes a plant virus CP. Exemplary coat proteins include, but are not limited to, the coat protein of tomato bushy stunt virus (TBSV), barley stripe mosaic virus (BSMV), red clovernecrotic mosaic virus (RCNMV), cucumber necrosis virus (CNV), tomato golden mosaic virus (TGMV), bean golden mosaic virus (BGMV), tomato leaf curl virus (TLCV), squash leaf curl virus (SqLCV), African cassava mosaic virus (ACMV), Potyvirus, squash mosaic virus, garlic virus A (Helguera et al., 1997), grape chrome mosaic virus (Torregrosa et al., 1997), potato virus Y and potato leaf roll virus (Zhang et al., 1997), rice dwarf virus (Zheng et al., 1997), beet necrotic yellow vein virus (Fecker et al., 1996), Montana barley yellow dwarf virus (Geske et al., 1996), papaya ringspot virus (Scorza et al., 1995), pea early-browning virus (MacFarlane et al., 1995), rice yellow mottle virus (Brugidou et al., 1995), apple and pear stem pitting virus (Jelkmann, 1994), lettuce infectious yellows virus, beet yellows virus and citrus tristeza virus (Klassen et al., 1994), potato virus X (Truve et al., 1993), plum pox virus (Ravelonandro et al., 1992), cymbidium mosaic and white clover mosaic virus (Chia et al., 1992), cucumber mosaic virus (Slightom, 1991), alfalfa mosaic virus (Neelman et al., 1991), cowpea chlorotic mottle virus (Allison et al., 1990), and brome mosaic virus (Sacher et al., 1989), tobacco mosaic virus, cauliflower mosaic virus, turnip yellow mosaic virus, tomato aspermy virus, beet necrotic yellow vein virus, turnip crinkle virus, tobacco rattle virus, cymbidium ringspot virus, cowpea chlorotic mottle virus, tobacco etch virus, beet western yellow virus, southern bean mosaic virus, sunn-hemp mosaic virus, tobacco etch virus, cowpea mosaic virus, maize streak virus, beet curly top virus, and tomato leaf curl virus (see, for example, Tables 1, 2 and 3 of Nelson and van Bel, 1998), the disclosure of which is incorporated by reference herein).

B. Other Sequences for in Plants

Expression of a preselected gene in plants can be enhanced by a number of elements or mechanisms, including the addition of promoters, enhancers, introns, leader sequences, and 3' sequences, as well as the replacement of native codons in a non-plant gene with codons that are preferred in plants curry et al., 1989; Perlak et al., 1991), and removal of AT-rich sequences, removal or alteration of cryptic poly A sequences, and removal or alteration of mRNA destabilizing sequences.

1. Promoters Enhancers, Introns, Leader Sequences and Other Regulatory Sequences Preferably, the preselected nucleic acid segment in a vector of the invention is operably linked to a promoter, which provides for expression of the preselected nucleic acid segment. The promoter is preferably a promoter functional in the host cell into which the vector is introduced, e.g., in plants and/or seeds. A preselected nucleic acid sequence is operably linked to the promoter when it is located downstream from the promoter.

Most genes have regions of nucleic acid that are known as promoters, which regulate gene expression. For genes encoded by genomic DNA, promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the Pa promoter can be induced to varying levels of gene expression depending on the level of isothiopropylgalactoside added to the transformed bacterial cells. Promoters can also provide for tissue specific or developmental regulation. An isolated promoter sequence that is a strong promoter for heterologous nucleic acid is advantageous because it provides for a sufficient level of gene expression to allow for easy detection and selection of transformed cells and provides for a high level of gene expression when desired.

Preferred plant promoters include, but are not limited to, a promoter such as the CaMV 35S promoter (Odell et al., 1985), an enhanced 35S promoter (Kay et al., 1987) or others such as CaMV 19S (Lawton et al., 1987), nos, AdhI (Walker et al., 1987), sucrose synthase (Yang et al., 1990), α-tubulin, ubiquitin, actin (Wang et al., 1992), cab (Sullivan et al., 1989), PEPCase (Hudspeth et al., 1989) or those associated With the R gene complex (Chandler et al., 1989). Further suitable promoters include the Z4 promoter from a gene encoding the Z4 22 kD α-zein protein, the Z10 promoter from a gene encoding a 10 kD zein protein, a Z27 promoter from a gene encoding a 27 kD zein protein, the A20 promoter from the gene encoding a 19 kD α-zein protein, inducible promoters, such as the light inducible promoter derived from the pea rbcS gene (Coruzzi et al., 1971) and the actin promoter from rice (McElroy et al., 1990); seed specific promoters, such as the phaseolin promoter from beans, may also be used (Sengupta-Gopalan, 1985). Other promoters useful in the practice of the invention are known to those of skill in the art.

A preselected nucleic acid, e.g., a DNA sequence, can be combined with the promoter by standard methods as described in Sambrook et al., cited supra, to yield an expression cassette. Briefly, a plasmid containing a promoter such as the 35S CaMV promoter can be constructed as described in Jefferson (1987) or obtained from Clontech Lab in Palo Alto, Calif. (e.g., pBI121 or pBI221). Typically, these plasmids are constructed to have multiple cloning sites having specificity for different restriction enzymes downstream from the promoter. The preselected DNA sequence can be subcloned downstream from the promoter using restriction enzymes and positioned to ensure that the DNA is inserted in proper orientation with respect to the promoter so that the DNA can be expressed as sense or antisense RNA. Once the preselected DNA sequence is operably linked to a promoter, the expression cassette so formed can be subcloned into a vector of the invention.

Once the preselected sense DNA sequence is obtained, all or a portion of the sequence can be subcloned into an expression vector (see below) in the opposite orientation (i.e., 3' to 5'). Similarly, all or a portion of the preselected DNA sequence can be subcloned in sense orientation (i.e., 5' to 3'). The preselected DNA sequence is subcloned downstream from a promoter to form an expression cassette.

Regulatory elements such as Adh intron 1 (Callis et al., 1987), sucrose synthase intron (Vasil et al., 1989) or TMV omega element (Gallie et al., 1989), as well as viral subgenomic sequences, e.g., viral subgenomic RNA sequences, may further be included where desired.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants are most preferred.

It is contemplated that vectors for use in accordance with the present invention may be constructed to include the ocs enhancer element. This element was first identified as a 16 bp palindromic enhancer from the octopine synthase (ocs) gene of agrobacterium, and is present in at least 10 other promoters (Bouchez et al., 1989). It is proposed that the use of an enhancer element, such as the ocs element and particularly multiple copies of the element, will act to increase the level of transcription from adjacent promoters.

Ultimately, the most desirable nucleic acid segments for introduction into a plant may be homologous genes or gene families which encode a desired trait (e.g., increased yield per acre) and which are introduced under the control of novel promoters or enhancers, etc., or perhaps even homologous tissue specific (e.g., root-, collar/sheath-, whorl-, stalk-, earshank-, kernel- or leaf-specific) promoters or control elements. Indeed, it is envisioned that a particular use of the present invention will be the targeting of a gene in a tissue-specific manner. For example, insect resistant genes may be expressed specifically in the whorl and collar/sheath tissues which are targets for the first and second broods, respectively, of ECB. Likewise, genes encoding proteins with particular activity against rootworm may be targeted directly to root tissues.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos, and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm. It is particularly contemplated that one may advantageously use the 16 bp ocs enhancer element from the octopine synthase (ocs) gene (Bonchez et al., 1989), especially when present in multiple copies, to achieve enhanced expression in roots.

It is also contemplated that tissue-specific expression may be functionally accomplished by introducing a constitutively expressed gene (all tissues) in combination with an antisense gene that is expressed only in those tissues where the gene product is not desired. For example, a gene coding for the crystal toxin protein from *B. thuringiensis* (*Bt*) may be introduced such that it is expressed in all tissues using the 35S promoter from Cauliflower Mosaic Virus. Expression of an antisense transcript of the *Bt* gene in a maize kernel, using for example a zein promoter, would prevent accumulation of the Bt protein in seed. Hence the protein encoded by the introduced gene would be present in all tissues except the kernel.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Preferably, one would like to identify a gene that is not present in a high copy number, but which gene product is relatively abundant in specific tissues. The promoter and control elements of corresponding genomic clones may then be localized using the techniques known to those of skill in the art.

It is contemplated that expression of some genes in transgenic plants will be desired only under specified conditions. For example, it is proposed that expression of certain genes that confer resistance to environmental stress factors such as drought will be desired only under actual stress conditions. It is contemplated that expression of such genes throughout a plant's development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It is also anticipated that expression of genes conferring resistance to insect predation would be desired only under conditions of actual insect infestation. Therefore, for some desired traits inducible expression of genes in transgenic plants will be desired.

It is proposed that in some embodiments of the present invention expression of a gene in a transgenic plant will be desired only in a certain time period during the development of the plant. Developmental timing is frequently correlated with tissue-specific gene expression. For example, expression of zein storage proteins is initiated in the endosperm about 15 days after pollination.

2.. Intracellular or Extracelluar Targeting Sequences

Additionally, expression cassettes can be constructed and employed to target the product of the preselected nucleic acid sequence or segment to an intracellular compartment within plant cells or to direct a protein to the extracellular environment. This can generally be achieved by joining a DNA sequence encoding a transit or signal peptide sequence to the coding sequence of the preselected DNA sequence. The resultant transit, or signal, peptide will transport the protein to a particular intracellular, or extracellular destination, respectively, and can then be post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

A particular example of such a use concerns the direction of a herbicide resistance gene, such as the EPSPS gene, to a particular organelle such as the chloroplast rather than to the cytoplasm. This is exemplified by the use of the rbcS transit peptide which confers plastid-specific targeting of proteins. In addition, it is proposed that it maybe desirable to target certain genes responsible for male sterility to the mitochondria, or to target genes for resistance to phytopathogenic organisms to the extracellular spaces, or to target proteins to the vacuole.

It is also contemplated that it may be useful to target DNA itself within a cell. For example, it may be useful to target introduced DNA to the nucleus as this may increase the frequency of transformation. Within the nucleus itself it would be useful to target a gene in order to achieve site-specific integration. For example, it would be useful to have a gene introduced through transformation replace an existing gene in the cell.

3. 3' Sequences

When the expression cassette is to be introduced into a plant cell, the expression cassette can also optionally include 3' nontranslated regulatory DNA sequences that act as a signal to terminate transcription and allow for the polyadenylation of the resultant mRNA. The 3' nontranslated regulatory DNA sequence preferably includes from about 50 to about 1,000, more preferably about 100 to about 1,000, nucleotide base pairs and contains plant transcriptional and translational termination sequences. Preferred 3' elements are derived from those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato, although other 3' elements known to those of skill in the art can also be employed. These 3' nontranslated regulatory sequences can be obtained as described in An (1987) or are already present in plasmids available from commercial sources such as Clontech, Palo Alto, Calif. The 3' nontranslated regulatory sequences can be operably linked to the 3' terminus of the preselected DNA sequence by standard methods.

4. Selectable or Screenable Markers

In order to improve the ability to identify transformants, one may desire to employ a selectable or screenable marker gene as, or in addition to, the preselected nucleic acid sequence or segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, and which polypeptide includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet, accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Stiefel et al., 1990) is preferred as this molecule is well characterized in terms of molecular biology, expression, and protein structure. However, any one of a variety of extensins and/or glycine-rich wall proteins (Keller et al., 1989) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant cell, e.g., a monocot cell.

Possible selectable markers for use in connection with the present invention include, but are not limited to, a neo gene (Potrykus et al., 1985) which codes for kanamycin resistance and can be selected for using kanamycin, G418, a gene encoding resistance to bleomycin, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon; or a mutated anthranilate synthase gene that confers resistance to 5-methyl tryptophan. Where a mutant EPSP synthase, gene is employed, additional benefit may be realized through the incorporation of a suitable chloroplast transit peptide, CTP (European Patent Application 0 218 571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyltransferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals (Potrykus, 1989).

Screenable markers that may be employed include, but are not limited to, a β-glucuronidase or uidA gene (GUS) which encodes an enzyme for which various, chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or an aequorin gene (Prasher et al., 1985), which may be employed in calcium-sensitive bioluminescence detection, or a green fluorescent protein gene (Niedz et al., 1995).

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3).

Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

5. Plasmid and Non-viral Vector Sequences

A vector of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An, cited supra, and is available from Dr. An. This binary Ti vector can be replicated in prokaryotic bacteria 'such as *E. coli* and Agrobacterium. The Agrobacterium plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

Virtually any DNA may be used for delivery to recipient cells to ultimately produce fertile transgenic plants in accordance with the present invention. For example, DNA segments in the form of vectors and plasmids, or linear DNA fragments, in some instance containing only the DNA element to be expressed in the plant, and the like, may be employed.

Vectors, plasmids, cosmids, YACs (yeast artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

6. Other Preselected Nucleic Acid Segments

A preferred embodiment of the invention provides a vector method for encoding a desirable agronomic property to a plant, such as single genes for improvement of traits related to crop production. For example, such nucleic acid segments or "genes" are disclosed, for example in Lundquist et al. (U.S. Pat. No. 5,484,956), Lundquist et al. (U.S. Pat. No. 5,508,468), Dobres (international application PCT/US95/11231) and by K. Weising et al. ((1988), see Tables 1, 2, and 3), all of which are incorporated by reference herein. However, the present invention is not limited in scope to preselected nucleic acid segments which encode a desirable agronomic property; as many other preselected nucleic acid segments which encode proteins or RNA transcripts that confer desirable characteristics to plants are within the scope of the invention.

The choice of the particular nucleic acid segments to be delivered to the recipient cells will often depend on the purpose of the transformation. One of the major purposes of transformation of crop plants is to add some commercially desirable, agronomically important traits to the plant. One may desire to incorporate one or more genes conferring any such desirable trait or traits, such as, for example, a gene or genes encoding herbicide resistance. Preferred agronomic properties encoded by the preselected DNA segment include, but are not limited to, insect resistance or tolerance, herbicide resistance or tolerance (Christou, 1997), disease resistance or tolerance (e.g., pathogen resistance in tobacco or potato, resistance to viruses, fungal or bacterial pathogens using, for example, Bt endotoxin genes. (Schell, 1997; Vaeck et al., 1987; and Lundquist et al., U.S. Pat. No. 5,484,956), Pht toxin secreted from *Photorhabdus luminescens*, or virus-derived proteins for viral resistance (Reimann-Phillip et al., 1993), environmental stresses including, but not limited to, drought, excess moisture, chilling, freezing, high temperature, salt, and oxidative stress, increased yields, food content and makeup, physical appearance, male sterility, drydown, standability, prolificacy, starch properties, oil quantity and quality; and the like. For example, genetic studies have shown that for a plant to resist infection by a particular plant pathogen, the plant must have a resistance (R) gene which interacts directly or indirectly with a single avirulence (avr) gene which is present in the genome of the pathogen. Thus, the introduction of a preselected DNA segment comprising a R gene into a plant which lacks the R gene can confer resistance to the plant to a pathogen which expresses the corresponding avr gene.

Enhanced resistance to fungal infections may be obtained by introducing a preselected DNA segment which encodes a pathogenesis related (PR) protein into a plant. PR proteins are proteins which are synthesized by cereals in response to infection by some pathogenic fungi (Scott, 1994). Other anti-fungal genes include, but are not limited to, chitinase (e.g., exo-chitinase and chitinase G); glucanase; protein-synthesis inhibitor (PSI) or antifungal protein (AFP)

Enhanced resistance to viral infections may be obtained by introducing a preselected DNA segment encoding a viral coat protein into a plant. For example, Nelson et al., (1988) disclose that the expression of the tobacco mosaic virus (TMV): coat protein in a tomato plant confers tolerance to the plant to TMV and to tomato mosaic virus (ToMV), a virus related to TMV. Clark et al. (International application PCT/EP92/03001) disclose that expression of maize dwarf mosaic virus coat protein in corn resulted in plants which exhibited reduced disease symptoms when exposed to the virus.

Moreover, it is envisioned that more than one preselected nucleic acid segment can be introduced into a plant. For example, a vector which contains a selectable marker gene and a gene which confers resistance to a particular virus, e.g., barley yellow dwarf virus, potato leaf roll virus, or tobacco mosaic virus, can be introduced into plant cells.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity or quality, or those increasing yield or nutritional quality may be employed as desired.

a. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP synthase), is normally inhibited by the herbicide N-(phosphonomethyl)glycine (glyphosate). However, genes are known to encode glyphosate-resistant EPSP synthase enzymes. These genes are particularly contemplated for use in monocot transformation. The deh gene encodes the enzyme dalapon dehalogenase and confers resistance to the herbicide dalapon. The bxn gene codes for a specific nitrilase enzyme that converts bromoxynil to a non-herbicidal degradation product.

h. Insect Resistance

An important aspect of the present invention concerns the introduction of insect resistance-conferring genes into monocotyledonous plants such as maize. Potential insect resistance genes which can be introduced include *Bacillus thuringiensis* crystal toxin genes or *Bt* genes (Watrud et al., 1985). Bt genes may provide resistance to lepidopteran or coleopteran pests such as European Corn Borer (ECB). Preferred *Bt* genes for use in such embodiments include the CrylA(b) and CrylA(c) genes. Endotoxin genes from other species of *B. thuringiensis* which affect insect growth or development may also be employed in this regard.

The poor expression of prokaryotic *Bt* toxin genes in plants is a well-documented phenomenon, and the use of different promoters, fusion proteins, and leader sequences has not led to significant increases in *Bt* protein expression (Barton et al., 1987). It is therefore contemplated that the most advantageous *Bt* genes for use in the transformation protocols disclosed herein will be those in which the coding sequence has been modified to effect increased expression in plants, and more particularly, those in which maize preferred codons have been used. Example of such modified *Bt* toxin genes include the variant *Bt* CrylA(b) gene termed IAb6 (Perlak et al., 1991) and the synthetic CrylA(c) genes termed 1800a and 1800b.

Protease inhibitors may also provide insect resistance (Johnson et al., 1989), and will thus have utility in maize transformation. The use of a protease inhibitor II gene, pinII, from tomato or potato is envisioned to be particularly useful. Even more advantageous is the use of a pinII gene in combination with a *Bt* toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB, and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, may also result in insecticidal activity, or perhaps cause cessation of metamorphosis (Hammock et al., 1990).

Transgenic maize expressing genes which encode enzymes that affect the integrity of the insect cuticle form yet another aspect of the invention. Such genes include those encoding, e.g., chitinase, proteases, lipases, and also genes for the production of nikkomycin, a compound that inhibits chitin synthesis, the introduction of any of which is contemplated to produce insect resistant maize plants. Genes that encode for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming maize to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway. The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including rootworm. It is anticipated that genes encoding proteins that are toxic to insects or are involved in the biosynthesis of compounds toxic to insects will be isolated from Tripsacum and that these novel genes will be useful in conferring resistance to insects. It is known that the basis of insect resistance in Tripsacum is genetic, because said resistance has been transferred to *Zea mays* via sexual crosses (Branson and Guss, 1972).

Further genes encoding proteins characterized as having potential insecticidal activity may also be used as transgenes in accordance herewith. Such genes include, for example, the cowpea trypsin inhibitor (CpTI; Hilder et al., 1987) which may be used as a rootworm deterrent; genes encoding avermectin (Avermectin and Abamectin., Campbell, W. C., Ed., 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can convert a non-toxic insecticide (pro-insecticide) applied to the outside of the plant into an insecticide inside the plant are also contemplated.

c. Environment or Stress Resistance

Improvement of corn's ability to tolerate various environmental stresses such as, but not limited to, drought, excess moisture, chilling, freezing, high temperature, salt, and oxidative stress, can also be effected through expression of novel genes. It is proposed that benefits may be realized in terms of increased resistance to freezing temperatures through the introduction of an "antifreeze" protein such as that of the Winter Flounder (Cutler et al., 1989) or synthetic gene derivatives thereof. Improved chilling tolerance may also be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plant's increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically active solutes may impart protection against drought. Within this class are genes encoding for mannitol dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993).

Similarly, the efficacy of other metabolites in protecting either enzyme function (e.g., alanopine or propionic acid or membrane integrity (e.g., alanopine) has been documented (Loomis et al., 1989), and therefore expression of genes encoding for the biosynthesis of these compounds might confer drought resistance in a manner similar to or complementary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), raffinose (Bernal-Lugo and Leopold, 1992), proline (Rensburg et al., 1993) and glycinebetaine (Wyn-Jones and Storey, 1982), ononitol and pinitol (Vernon and Bohnert, 1992). Continued canopy growth and increased reproductive fitness during times of stress will be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure et al., 1989). All three classes of LEAs have been demonstrated in maturing (i.e., desiccating) seeds. Within these 3 types of LEA proteins, the Type-II (dehydrin-type) have generally been implicated in drought and/or desiccation tolerance in vegetative plant parts (i.e., Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It is also contemplated that genes that effect lipid biosynthesis and hence membrane composition might also be useful in conferring drought resistance on the plant.

Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1987 and Shagan et al., 1993 which are incorporated herein by reference). Spatial and temporal expression patterns of these genes may enable corn to better withstand stress.

It is proposed that expression of genes that are involved with specific morphological traits that allow for increased water extractions from drying soil would be of benefit. For example, introduction and expression of genes that alter root characteristics may enhance water uptake. It is also contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn to utilize water more efficiently, through the introduction and expression of novel genes, will improve overall performance even when soil water availability is not limiting. By introducing genes that improve the ability of corn to maximize water usage across a full range of stresses relating to water availability, yield stability or consistency of yield performance may be realized.

d. Disease Resistance

It is proposed that increased resistance to diseases may be realized through introduction of genes into monocotyledonous plants such as maize. It is possible to produce resistance to diseases caused by viruses, bacteria, fungi and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotic are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes proteins (Bol, Linthorst, and Comelissen, 1990). Included amongst the PR proteins are β-1, 3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It is also contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics.

Plant parasitic nematodes are a cause of disease in many plants, including maize. It is proposed that it would be possible to make the corn plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

e. Mycotoxin Reduction/Elimination

Production of mycotoxins; including aflatoxin and fumonisin, by fungi associated with monocotyledonous plants such as maize is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. It is also proposed that it may be possible to introduce novel genes into monocotyledonous plants such as maize that would inhibit synthesis of the mycotoxin without interfering with fungal growth. Further, it is contemplated that expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

f. Grain Composition or Quality

Genes may be introduced into monocotyledonous plants, particularly commercially important cereals such as maize, to improve the grain for which the cereal is primarily grown. A wide range of novel transgenic plants produced in this manner may be envisioned depending on the particular end use of the grain.

The largest use of maize grain is for feed or food. Introduction of genes that alter the composition of the grain may greatly enhance the feed or food value. The primary composition of maize grain are starch, protein, and oil. Each of these primary components of maize grain may be improved by altering its level or composition. Several examples may be mentioned for illustrative purposes but in no way provide an exhaustive list of all possibilities.

The protein of cereal grains including maize is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase the transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Example may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It is also proposed that the protein composition of the grain may be modified through the phenomenon of cosuppression, i.e., inhibition of expression of an endogenous gene through the expression of an identical structural gene or gene fragment introduced through transformation (Goring et al., 1991). Additionally, the introduced DNA may encode enzymes which degrade zeins. The decreases in zein expression that are achieved may be accompanied by increases in proteins with more desirable amino acid composition or increases in other seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable-energy-content and -density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising primarily maize or other cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorous, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of maize or other cereals for feed and food purposes might be described. The improvement may not even necessarily involve the grain, but may, for example, improve the value of the corn for silage. Introduction of DNA to accomplish this might include sequences that alter lignin production such as those that result in the "brown midrib" phenotype associated with superior feed value for cattle.

In addition to direct improvement in feed or food value, genes may also be introduced which improve the processing of corn and improve the value of the products resulting from the processing. The primary method of processing corn is via wetmilling. Maize may be improved through the expression of novel genes that increase the efficiency and reduce the cost of processing such as by decreasing steeping time.

Improving the value of wetmilling products may include altering the quantity or quality of starch, oil, corn gluten meal; or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or in combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturates, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic acid and oleic acids. Another example is the blockage of elongation steps resulting in the accumulation of $c_8$ to $c_{12}$ saturated fatty acids.

Improvements in the other major corn wetmilling products, corn gluten meal and corn gluten feed, may also be achieved by the introduction of genes to obtain novel corn plants. Representative possibilities include but are not limited to those described above for improvement of food and feed value.

In addition it may further be considered that the corn plant be used for the production or manufacturing of useful biological compounds that were either not produced at all, or not produced at the same level, in the corn plant previously. The novel corn plants producing these compounds are made possible by the introduction and expression of genes by corn transformation methods. The vast array of possibilities include but are not limited to any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses through introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

g. Plant Agronomic Characteristics

Two of the factors determining where corn can be grown are the average daily temperature during the growing season and the length of time between frosts. Within the areas where it is possible to grow corn, there are varying limitations on the maximal time it is allowed to grow to maturity and be harvested. The corn to be grown in a particular area is selected for its ability to mature and dry down to harvestable moisture content within the required period of time with maximum possible yield. Therefore, corn of varying maturities is developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. It is considered that genes that influence maturity and/or dry down can be identified and introduced into corn lines using transformation techniques to create new corn varieties adapted to different growing locations or the same growing location but have improved yield-to-moisture ratio at harvest. Expression of genes that are involved in regulation of plant development may be especially useful, e.g., the liguleless and rough sheath genes that have been identified in corn.

It is contemplated that genes may be introduced into corn that would improve standability and other plant growth characteristics. Expression of novel genes which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. It is proposed that overexpression of genes within corn that are associated with "stay green" or the expression of any gene that delays senescence would be advantageous. For example, a nonyellowing mutant has been identified in *Festuca pratensis* (Davies et al., 1990).

Expression of this gene as well as others may prevent premature breakdown of chlorophyll and thus maintain canopy function.

h. Nutrient Utilization

The ability to utilize available nutrients may be a limiting factor in growth of monocotyledonous plants such as maize. It is proposed that it would be possible to alter nutrient uptake, tolerate pH extremes, mobilization through the plant, storage pools, and availability for metabolic activities by the introduction of novel genes. These modifications would allow a plant such as maize to more effectively utilize available nutrients. It is contemplated that an increase in the activity of, for example, an enzyme that is normally present in the plant and involved in nutrient utilization would increase the availability of a nutrient; An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

i. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlated with T cytoplasm. It is proposed that it would be possible through the introduction of TURF-13 via transformation to separate male sterility from disease sensitivity. As it is necessary to be able to restore male fertility for breeding purposes and for grain production it is proposed that genes encoding restoration of male fertility may also be introduced.

j. Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding a Bt gene that confers insect resistance on the plant may be introduced into a plant together with a bar gene that is useful as a selectable marker and confers resistance to the herbicide Ignite® on the plant. However, it may not be desirable to have an insect resistant plant that is also resistant to the herbicide Ignite®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

It is also contemplated that a negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (nptII) has been investigated as a negative selectable marker in tobacco (*Nicotiana tabacum*) and *Arabidopsis thaliana* (Xiang, C. and Guerra, D. J. 1993). In this example both sense and antisense npt II genes are introduced into a plant through transformation and the resultant plants are sensitive to the antibiotic kanamycin. An introduced gene that integrates into the host cell chromosome at the site of the antisense nptII gene, and inactivates the antisense gene, will make the plant resistant to kanamycin and other aminoglycoside antibiotics. Therefore, rare site-specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers may also be useful in other ways. One application is to construct transgenic lines in which one could select for transposition to unlinked sites. In the process of tagging, it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, J., 1993). In the presence of this enzyme, the compound 5-fluorocytosine is converted to 5-fluorouracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthlene acetamide (NAM) to α-naphthlene acetic acid (NAA) renders plant cells sensitive to high concentrations of NAM.

It is also contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

k. Non-protein-expressing Sequences

1. RNA-expressing

Nucleic acid may be introduced into corn and other monocots for the purpose of expressing RNA transcripts that function to affect plant phenotype yet are not translated into protein. Two example are antisense RNA and RNA with ribozyme activity. Both may serve possible function in reducing or eliminating expression of native or introduced plant genes.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring et al., 1991; Smith et al., 1990; Napoli, C. et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of level of that native protein.

2. Non-RNA-expressing

For example, DNA elements including those of transposable elements such as Ds, Ac, or Mu, may be inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of the gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabeled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependant effects upon incorporation into the plant genome (Stief et al., 1989; Phi-Van et al., 1990).

Expression of novel preselected DNA segments that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a preselected DNA segment encoding the biosynthesis of osmotically-active solutes can impart protection against drought. Within this class of preselected DNA segments are DNAs encoding mannitol dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced preselected DNAs will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., cited supra (1992), (1993)).

Similarly, the efficacy of other metabolites in protecting either enzyme function (e.g. alanopine or propionic acid) or membrane integrity (e.g., alanopine) has been documented (Loomis et al., 1989), and therefore expression of a preselected DNA segment encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson et al., 1992); sorbitol, dulcitol (Karsten et al., 1992); glucosylglycerol (Reed et al., 1984); Erdmann et al., 1992); sucrose, stachyose (Koster and Leopold, 1988); (Blackman et al., 1992); ononitol and pinitol (Vernon and Bohnert, (1992); and raffinose (Bernal-Lugo and Leopold, 1992). Other osmotically active solutes which are not sugars include, but are not limited to, proline (Rensburg et al., 1993) and glycine-betaine (Wyn-Jones and Storey, 1981). Continued canopy growth and increased reproductive fitness during times of stress can be augmented by introduction and expression of preselected DNA segments such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure et al., 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (i.e., Mundy and Chua, (1988); Piatkowski et al., (1990); Yamaguchi-Shinozaki et al., (1992). Recently, expression of a Type-III LEA (HVA-1) in tobacco was found to influence plant height, maturity and drought tolerance (Fitzpatrick, (1993). Expression of structural genes from all three groups may therefore confer drought tolerance. Other types of proteins induced during water stress include thiol proteases, aldolases and transmembrane transporters (Guerrero et al., 1990), which may confer various protective and/or repair-type functions during drought stress. The expression of a preselected DNA segment that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al. (1990) and Shagan et al., (1993), which are incorporated herein by reference). Spatial and temporal expression patterns of these genes may enable maize to better withstand stress.

It is proposed that expression of genes that are involved with specific morphological traits that allow for increased water extractions from drying soil would be of benefit. For example, introduction and expression of genes that alter root characteristics may enhance water uptake. It is also contemplated that expression of DNAs that enhance reproductive fitness during times of stress would be of significant value. For example, expression of DNAs that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value. It is further contemplated that regulation of cytokinin levels in monocots, such as maize, by introduction and expression of an isopentenyl transferase gene with appropriate regulatory sequences can improve monocot stress resistance and yield (Gan et al., *Science*, 270, 1986 (1995)).

Given the overall role of water in determining yield, it is contemplated that enabling maize to utilize water more efficiently, through the introduction and expression of novel genes, will improve overall performance even when soil water availability is not limiting. By introducing genes that improve the ability of maize to maximize water usage across a full range of stresses relating to water availability, yield stability or consistency of yield performance may be realized.

III. Introduction of a Vector of the Invention to a Host Cell

The present invention generally includes steps directed to introducing a preselected nucleic acid sequence into a recipient cell, e.g., a plant cell, to create a transformed cell. Although is it preferred that the vector or composition of the invention is contacted with a plant, plant part or plant tissue by spraying or rubbing, the vector or composition can be introduced to plant cells in vitro by other methods. For this purpose, cells of the plant tissue source are preferably embryogenic cells or cell-lines that can regenerate fertile transgenic plants and/or seeds. The cells can be derived from either monocotyledons or dicotyledons. Suitable examples of plant species include wheat, rice, Arabidopsis, tobacco, maize, soybean, and the like. The preferred cell type is a monocotyledon cell such as a maize cell, which may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: transformation by direct DNA transfer into plant cells by electroporation (U.S. Pat. No. 5,384,253 and U.S. Pat. No. 5,472,869, incorporated herein by reference; Dekeyser et al., 1990); direct DNA transfer to plant cells by PEG precipitation (Hayashimoto et al., 1990); direct DNA transfer to plant cells by microprojectile bombardment (McCabe et al., 1988; Gordon-Kamm et al., 1990; U.S. Pat. No. 5,489,520; U.S. Pat. No. 5,538,877; and U.S. Pat. No. 5,538,880, incorporated herein by reference); liposomes; and DNA transfer to plant cells via infection with Agrobacterium. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

A preferred method for dicot transformation is via infection of plant cells with *Agrobacterium tumefaciens* using the leaf-disk protocol (Horsch et al., 1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. No. 5,384,253; and U.S. Pat. No. 5,472,869). For example, embryogenic cell lines derived from immature *Zea mays* embryos can be transformed by accelerated particle treatment as described by Gordon-Kamm et al. (1990) or U.S. Pat. No. 5,489,520; U.S. Pat. No. 5,538,877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. It is also contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., 1988), the formation of partially degraded cells, or the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., 1990). The screen disperses the particles so that they are not delivered to the recipient cells in large aggregates. It is believed that a screen intervening between the projectile. apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 now abandoned and PCT publication WO 95/06128 (incorporated herein by reference).

The transformation is carried out under conditions directed to the plant tissue of choice. The plant cells or tissue are exposed to the DNA carrying the preselected DNA sequences for an effective period of time. This may range from a less-than-one-second pulse of electricity for electroporation to a 2–3 day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

A preferred method to transfer a preselected nucleic acid sequence to a plant is by spraying or rubbing a plant or plant part with a composition of the invention. Preferred monocot plants include sweet corn, oat, rice, maize, wheat, alfalfa, clover, fescue, sorghum, millet, barley, rye, or timothy grass. Preferred dicot plants include brassica, cucumber, tobacco, potato, tomato, rape, strawberry, soybean, sunflower, arabidopsis, petunia, pea, canola, bean, lettuce, spinach, alfalfa, cotton, lupins and carrot.

IV. Detection of Preselected Nucleic Acid Segments

To confirm the presence of the preselected nucleic acid segment(s) or "transgene(s)" in the regenerating plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transfornants have exogenous genes introduced into different sites in the genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer et al., 1992); Laursen et al., 1994) indicating stable inheritance of the gene. The nonchimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of preselected DNA segments encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

The transgenic plants produced herein are expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the preselected DNA segment may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The invention will be further described by the following examples which are not intended to limit the scope of the invention.

EXAMPLE 1

FHV-based Expression Vector for Local or Systemic Spread in Plants

Figure 8:
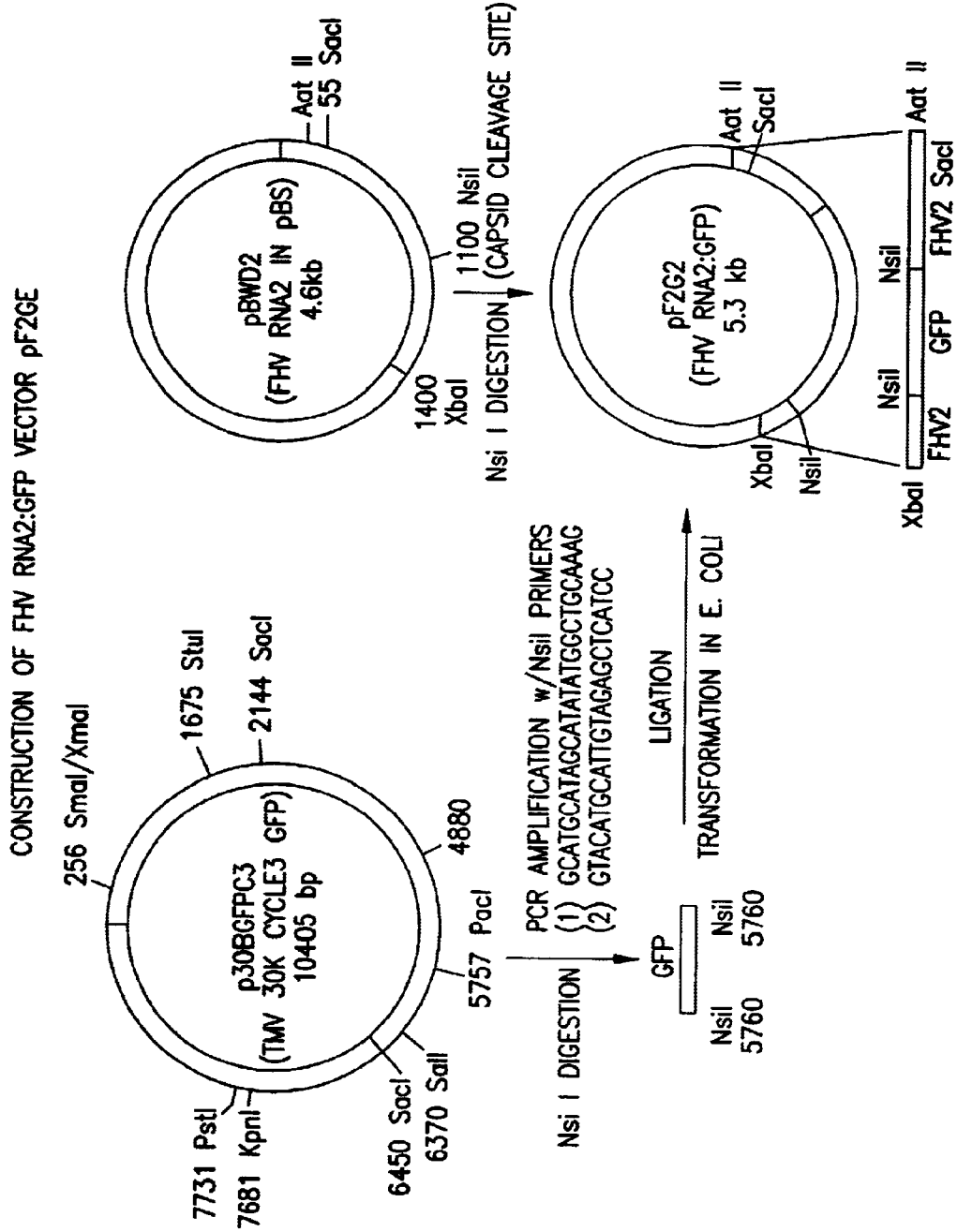
FIG. 8: Construction of a Nodavirus RNA-2 based vector encoding green fluorescent protein (GFP). GFP sequence is amplified from TMV cDNA clone p30BGFPC3 by PCR using primers (SEQ ID NOs:7–8) containing NsiI sites. Digestion of this PCR product and FHV cDNA clone pBWD2 with NsiI followed by ligation and transformation yields FHV RNA-2:GFP chimera pF2G3. Nucleotide positions and unique restriction sites are shown.

To overcome the problems associated with the existing plant virus-based vectors and develop a highly efficient viral vector system for gene expression in plants, a Nodavirus-based vector was prepared. The vector (FIG. 8) includes FHV RNA-2 sequences in which a marker gene called green fluorescence protein (GFP; Epel et al., 1996; Casper et al., 1996) was introduced in the cleavage site (beta/gamma, FIG. 1) of the capsid precursor so that the expression and movement of FHV or a nucleoprotein complex of FHV RNAs-:FHV coat protein:GFP could be monitored by measuring green fluorescence in inoculated leaves at different time intervals. GFP is a protein of 238 amino acid residues originally isolated from the jellyfish *Aquorea Victoria* (*Av*). It absorbs blue light with maximal absorption at 395 nm and emits green light with peak emission at 509 nm. When GFP is expressed in either prokaryotic or eukaryotic cells, it is capable of producing a strong green fluorescence when excited by the blue light (ultraviolet light) and this fluorescence requires no additional gene products, from its host. To construct the vector pF2G3 (FIG. 8), a cDNA clone of FHV RNA-2 (pBW2) in the Bluescript phagemid vector (Stratagene, Calif.) was used. The plasmid was opened at the cleavage site with the restriction enzyme NsiI. The GFP (cycle 3 GFP, 707 bp, optimized for expression in plants) sequence was PCR amplified from a TMV cDNA clone p30BGFPC3 (containing TMV RNA sequences plus GFP sequences in pUC19 phagemid vector) using specific primers containing NsiI sites. The PCR product was purified and inserted in the NsiI sites of pBWD2 (FIG. 8).

Two week old *Nicotiana benthamiana* plants, both wild type (TRS1) and transgenic expressing TMV MP (H3NB3) or RCNMV MP, were inoculated with 100 $\mu$l of 10 ng/$\mu$l FHV RNA or with 100 $\mu$l of 50 ng/$\mu$l RNA transcripts prepared from pF2G3 plus 10 ng/$\mu$l FHV RNA-1 as a source of FHV replicase. In vitro transcribed RNAS were prepared from the vector DNA using T3 or T7 RNA polymerase. TMV MP transgenic *N. benthamiana* plants were employed as it had been determined that the inoculation of transgenic *N. benthamiana* plants expressing TMV MP with FHV RNAs resulted in a 100-fold higher level of FHV accumulation in transgenic *N. benthamiana* leaves compared to controls (FIG. 17). This result suggested that TMV MP facilitates cell-to-cell movement of FHV. RT-PCR of total RNA confirmed this result.

Plants were grown in a growth chamber at 23–25° C. with a 12 hour light period. A control experiment was run in parallel where leaves were inoculated with RNA transcripts made from p30BGFPC3. Leaves were monitored for the synthesis of FHV RNAs as well as GFP by (1) reverse transcription-polymerase chain reaction (RT-PCR) of total RNA extracted from leaves, and by (2) green flourescence measurement at different time intervals by shining hand-held UTV lamps on leaves.

Figure 12:
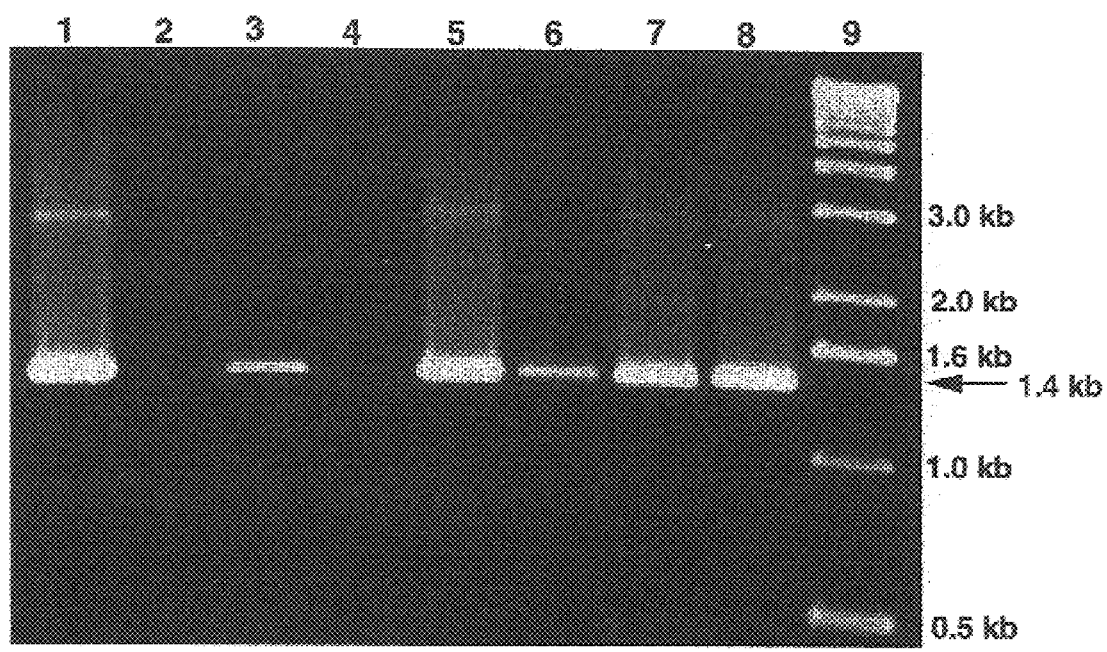
FIG. 12: RT-PCR of RNAs extracted from inoculated and secondary *N. benthamiana* leaves of TMV MP- or RCNMV MP-transgenic plants. Lane 1; purified FHV RNA-2 (800 ng) used as a template. Lane 2; mock (buffer) inoculated leaf. Lane 3; inoculated leaf of wild-type (non-transgenic) plant. Lane 4; uninoculated secondary leaf of wild type plant. Lane 5; inoculated leaf of TMV MP transgenic plant. Lane 6; uninoculated secondary leaf of TMV MP transgenic plant. Lane 7; inoculated leaf of RCNMV MP transgenic plant. Lane 8; uninoculated secondary leaf of RCNMV MP transgenic plant. Lane 9; marker. Arrow indicates PCR products corresponding to full length FHV RNA-2 (1.4 kb). Both TMV MP and RCNMV MP mobilized FHV to uninoculated secondary leaves.

Leaves were harvested 15 days after inoculation and total RNAs were extracted from 100 mg leaves (frozen in liquid nitrogen) by homogenization followed by hot phenol extraction (Verwoerd et al., 1989). Reverse transcription (RT) to cDNA and amplification by PCR were performed with SuperscriptII (Gibco/BRL, Bethesda, Md.) and Taq polymerase (Promega, Madison, Wis.), respectively. RT reactions were conducted at 42° C. for 1 hour. The cycling parameters for PCR were: 1 minute at 94° C., followed by 35 cycles of 94° C. for 30 seconds, 55° C. for 1 minute, 72° C. for 1.5 minutes, and then one cycle of 72° C. for 2 minutes. The primers employed were FHV2R1400 (SEQ ID NO:1; ACCTTAGTCTGTTGAC) and FHV2F1 (SEQ ID NO:2; GTAAACAATTCCAAG). PCR products were subjected to electrophoresis on 1% agarose gels (FIG. 12).

As described above, a 100-fold increase in the titer of FHV in TMV MP transgenic plants had been observed. This result was confirmed by RT-PCR analysis of RNA from inoculated TMV MP- and RCNMV MP-transgenic plants. Both TMV MP and RCNMV MP mobilized FHV to the uninoculated secondary leaves (FIG. 12, lanes 5–8). In non-transgenic plants, FHV sequences were only detected in the inoculated leaf not in the uninoculated secondary leaves (FIG. 12, lanes 3 and 4). When the synthesis of FHV RNA was monitored at different times post-inoculation, the presence of FHV sequences in wild type plants peaked at 7 dpi, but it was practically undetectable at 14 and 21 dpi. This was likely due to the inactivation of virus or viral nucleoprotein in absence of cell-to-cell movement. In transgenic plants, however, synthesis continued from 10 until 21 dpi due to movement of FHV through the inoculated leaf. Inoculation of half leaves with FHV RNAs followed by monitoring by RT-PCR also showed that FHV sequences moved to the uninoculated half in transgenic plants but very poorly compared to that of wild type plants. The presence of FHV sequences in plants by RT-PCR was determined using primers specific for FHV RNA-1 as well as FHV RNA-2.

Figure 7:
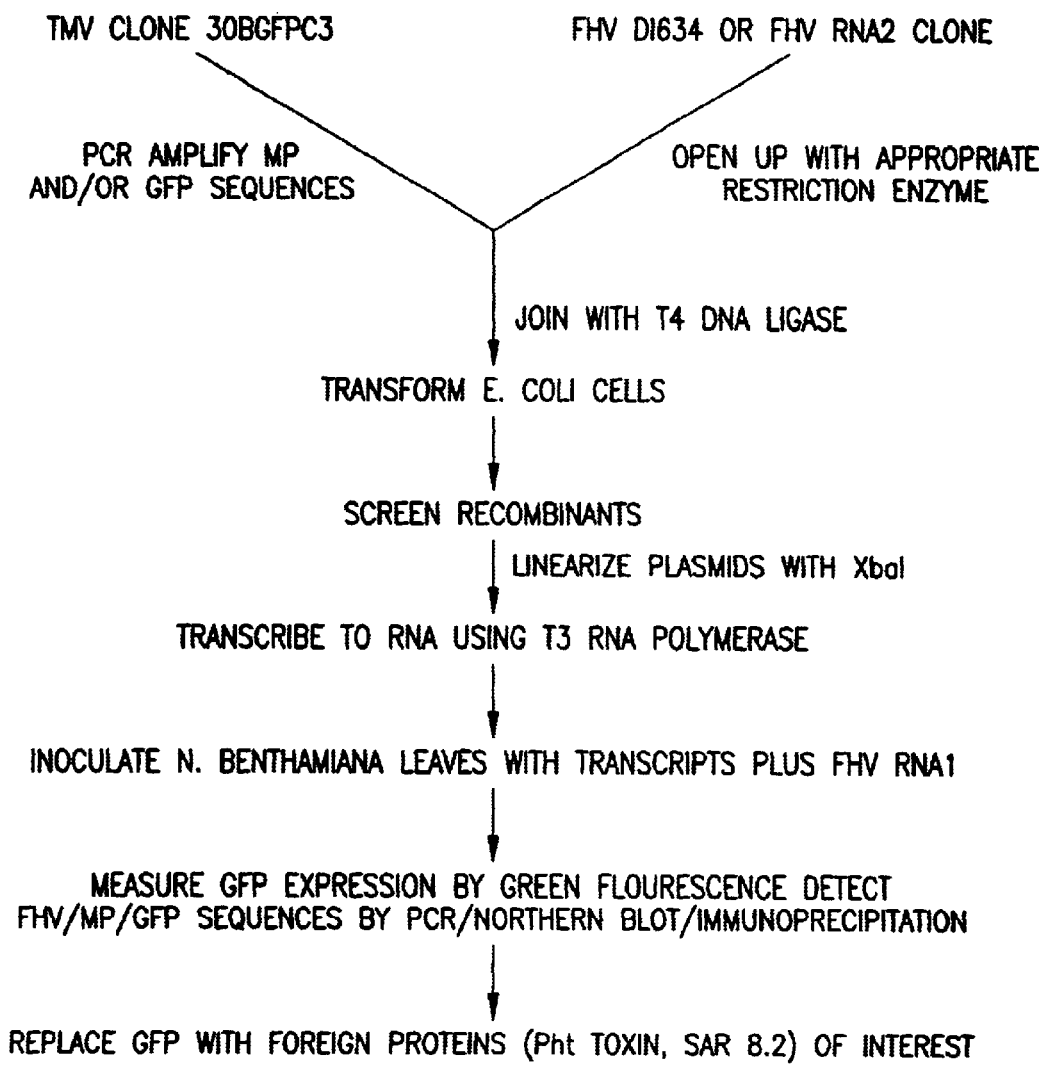
FIG. 7: General strategy for vector construction, RNA preparation, inoculation and detection.
Figure 9:
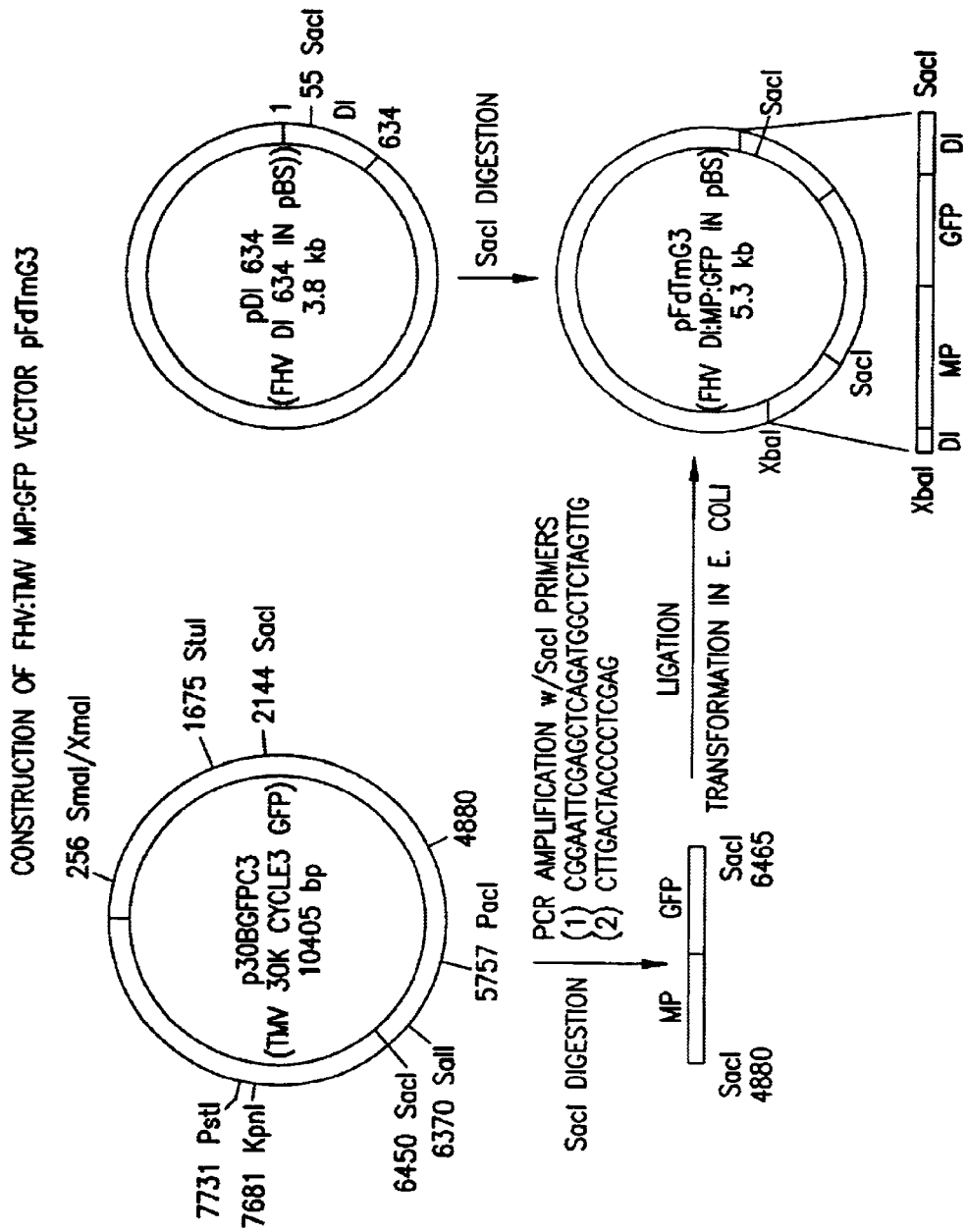
FIG. 9: Construction of a Nodavirus DI-based vector encoding Tobacco Mosaic Virus movement protein (TMV MP) and GFP. GFP and MP sequences are amplified from TMV cDNA clone p30BGFPC3 by PCR using primers (SEQ ID NOs:9–10) containing SacI sites. Digestion of this PCR product and FHV DI cDNA clone pD1634 with SacI followed by ligation and transformation yields FHV DI:TMV MP:GFP chimera pFdTmG3. Nucleotide positions and unique restriction sites are shown.
Figure 13A:
FIG. 13A: Leaf of *N. benthamiana* plant expressing GFP. A two week old transgenic plant expressing TMV MP was inoculated with 1 μg. RNA transcripts from the TMV expression vector 30BGFPC3 (a 10. 4 kb plasmid containing TMV replicase, the 30 kDa MP, GFP and CP). Ten days after inoculation the plant was: placed in between two long wave UV-lamps and photographs were taken with a Sony 3CCD color video camera (model DXC-960MD).
Figure 14:
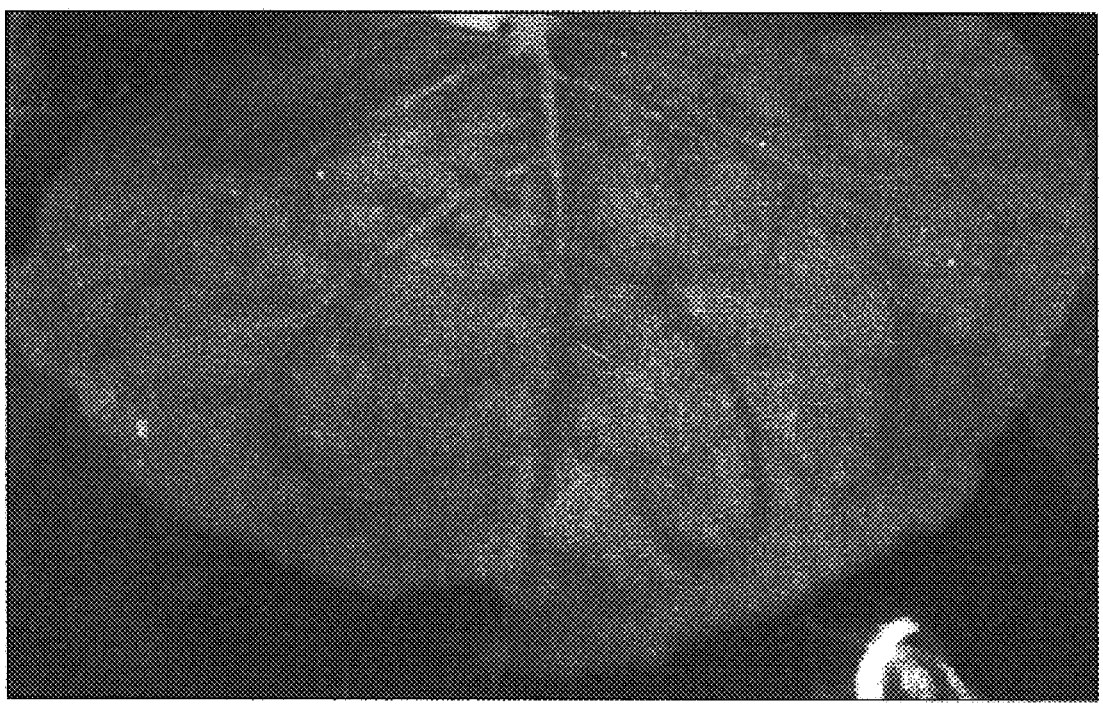
FIG. 14: Leaf of uninoculated *N. benthamiana* plant grown and photographed under the same conditions as described in FIG. 13. Note that the leaves appear violet due to the UV light but no green fluorescence was observed.

Measurement of GFP by green fluorescence showed small areas of patchy green fluorescence in leaves inoculated with RNA transcripts made from F2G3 (see FIG. 8) starting from day 10 dpi. In contrast, the non-inoculated plant did not show any such fluorescence. Vectors capable of high GFP expression, e.g., vectors based on FHV DI 634, have been constructed (FIGS. 7 and 9). Green fluorescence development (as shown in FIG. 13, a leaf from a plant inoculated with RNA transcripts from 30BGFPC3; compare with the uninoculated leaf in FIG. 14) with these constructs are evidence that FHV sequences as well as MP and GFP are expressed in such plants.

Long-distance movement of plant viruses through the plant has been shown to be dependent on coat proteins. Therefore, the systemic spread of the FHV-based vector can be further enhanced by introducing the coat protein (CP) of a plant virus into the vector. The CP of Red Clover Necrotic Mosaic Virus (RCNMV), a plant virus having genome strategy similar to FHV can thus be introduced into pF2TmG3 resulting in pFdTmRcG3 (FIG. 10). RCNMV is a spherical plant virus whose genome is divided in two messenger RNAs (Xiong et al., 1993). RCNMV RNA-1 (3.9 kb) codes for the coat protein (CP, 37 kDa) and RNA-2 (1.5 kb) codes for the RCNMV movement protein (35 kDa).

TMV MP, RCNMV CP and GFP sequences in the FHV-based vectors can be expressed as fusion proteins. Alternatively, proteolytic cleavage sequences can be introduced between these genes so that the expressed proteins are processed into individual proteins post-translationally. Initially, GFP sequences are placed at the 3'-end so that GFP expression is an indication of complete expression of the upstream sequences (i.e., TMV MP and RCNMV CP). However, the invention is not limited to any particular order of the introduced genes.

EXAMPLE 2

Use of a FHV-based Vector to Introduce Disease Resistance to Plants

Systemic Acquired Resistance (SAR) is one of the many mechanisms that plants use to resist pathogen infection. In tobacco, nine gene families that encode pathogen-related (PR) proteins are coordinately induced during SAR (for a review see Ryals et al., 1996). Certain SAR-related proteins (PR1 a and SAR 8.2) have been shown to suppress plant diseases in tobacco caused by the oomycetes *Phytophthora parasitica* (Alexander et al., 1992; Alexander et al., 1993, Alexander et al., 1993) and *Pythium torulosum*. Thus, the introduction of SAR-related proteins via a vector of the invention to tobacco, or to potato, may be useful to suppress or prevent plant diseases in tobacco or potato (e.g., late blight disease which is caused by *Phytophthora infestans*) caused by the oomycetes.

Figure 15:
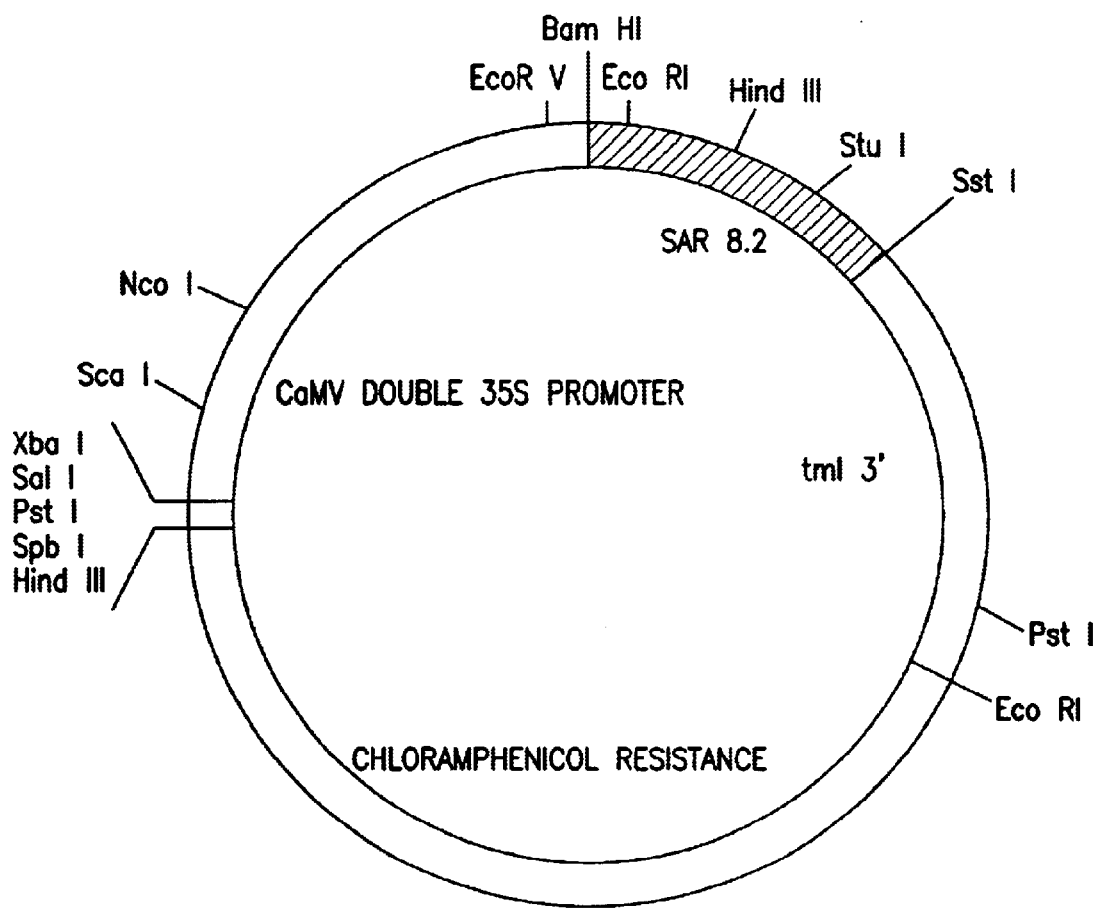
FIG. 15: Map of pCGN1788A, a plasmid containing systemic acquired resistance gene SAR 8.2. The BamHI-SstI fragment (529 bp) is introduced into FHV-based vector pFdTmRcG3.

To introduce SAR genes into a vector of the invention, a cDNA clone of the SAR 8.2 gene in a plasmid (PCGN1788A) with known sequence and restriction sites (FIG. 15) can be employed. A BamHI-SstI fragment from this plasmid containing the SAR 8.2 gene (529 bp) is PCR amplified and the PCR product is ligated into a FHV-based vector. Tobacco or potato leaves of 3–6 weeks old plants are cotransfected with RNA derived from the vector and FHV RNA-1. Expression of a CP:MP:SAR8.2:GFP fusion protein is monitored at regular intervals by fluorescence measurement and RT-PCR. At the onset of SAR expression, plants are inoculated by drenching of soil or spraying of leaves with Pythium or Phytophthora zoospores (300 spores per ml) in distilled water (Alexander et al., 1993; Chen et al., 1996). Control plants which are not transfected with the FHV-SAR8.2 chimera are also inoculated with zoospores in a similar way. Infected plants are kept for 7–9 days in a greenhouse maintained at a temperature of 23–25° C. with a 12-hour light period and compared for the suppression of disease symptoms such as damping-off, wilting or stunting.

EXAMPLE 3

The Use of a FHV-derived Vector for Domain Mapping of an Insecticidal Protein

Figure 16:
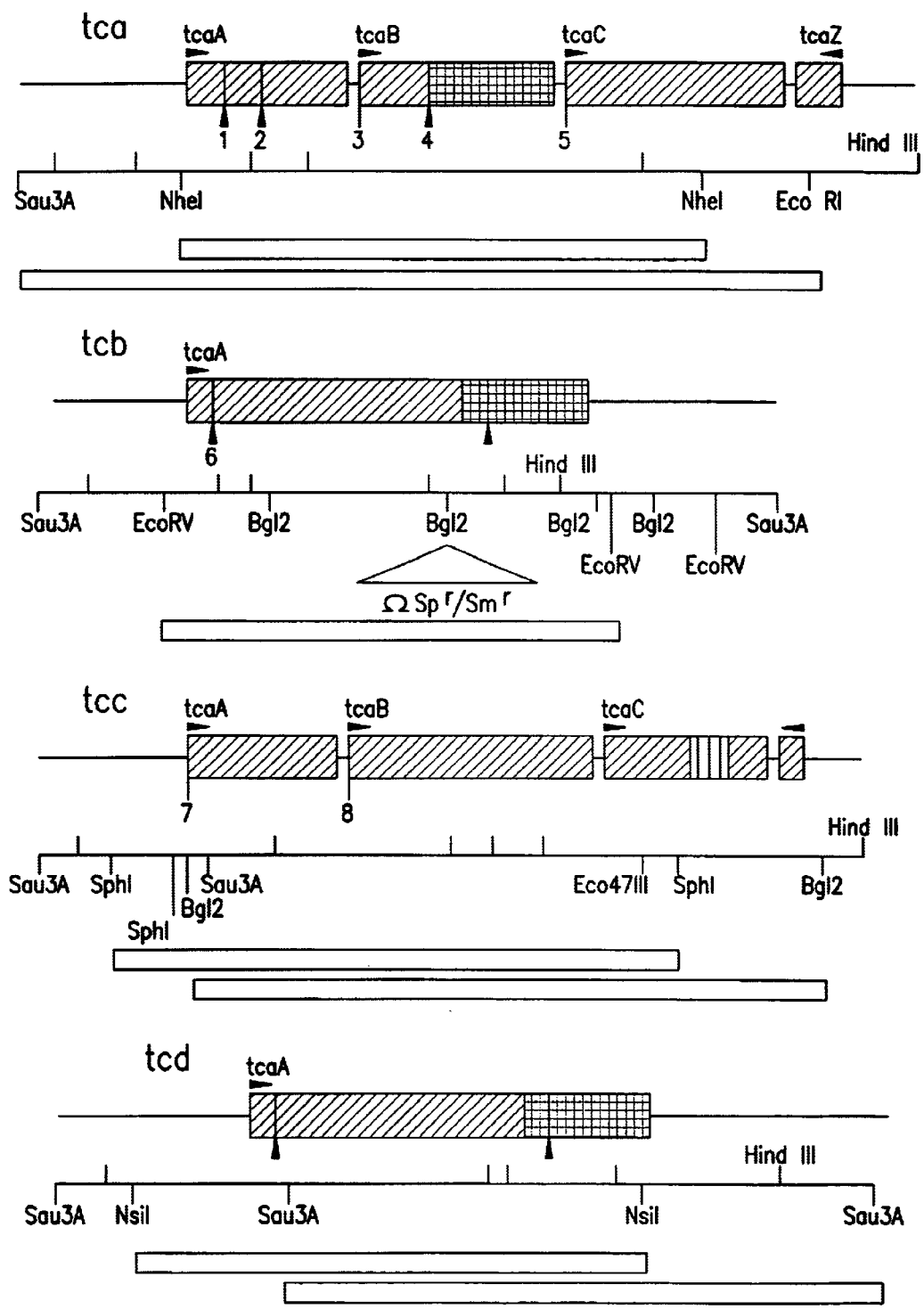
FIG. 16: Map of the four Photorhabdus toxin (Pht) loci: tca, tcb, tcc and tcd. Restriction sites used for gene disruption are shown below each locus. Shading indicates the regions of similarity between TcaB, TcbA and Tcdk that surround the presumptive protease cleavage sites. Fragments from loci tca and tcd (Bowen et al., 1998) are subcloned into our FHV-based vector pFdTmRcG3 and tested for toxicity.

The emerging field of functional genomics demands high through-put systems for testing the putative biological functions of coding and gene regulatory sequences. Three techniques for which genomics are particularly useful include antisense knockout, RNA interference (cosuppression) and domain mapping of large genes (Briggs et al., 1997; McKusick, 1997; Evans et al., 1997). Four Pht (an insecticidal protein secreted by the bacterium *Photorhabdus luminescens*) genes, 7–10 kb long, have been associated with toxin properties but the minimal sequences necessary for toxicity have not been identified. The genetic map of the four toxin complex loci tca, tcb, tcc and tcd are known (FIG. 16). To determine which regions of these genes are necessary for toxicity, specific sequences of the Pht genes, and combinations thereof, are introduced in an FHV-based vector to screen for functional domains of Pht (Bowen et al., 1998). In particular, as deletion of tca and tcd has been shown to abolish toxicity (Bowen, 1998), these genes are subcloned into an FHV-derived vector. Initially, approximately 500–1500 bp fragments of tca and tcd genes produced by partial or complete restriction digestion are introduced into the vector. *N. benthamiana* plants are inoculated with the RNA transcripts made from these constructs and the expression of the toxin genes monitored by feeding parts of plants to insects (*Manduca sexta*), followed by measuring the decrease in weight of the insects within 48 hours.

EXAMPLE 4

The Use of Vectors of the Invention for Insect Functional Genomics

In order to employ insect cell lines or insects as hosts for the vectors of the invention, modified viruses, modified insect cell lines or non-native insect hosts, e.g., fruit flies, are selected for resistance to cytopathic effect, i.e., lysis, after infection or transfection. Attenuation of the virus by mutation or by multiple passaging is one approach. Another approach is to select for cell lines that survive lysis. Approximately 1% of Drosophila cells survive lysis after infection by FHV and become persistently infected. Surviving cells carry FHV, are resistant to superinfection by nodaviruses and are capable of multiplying in fresh cells (Dasgupta et al., 1994). Sequence analysis of the FHV genomic RNAs showed no mutation in the viral genomes during the establishment of persistent infection, indicating that modification in Drosophila cells (1% of the total population), not in the viral genome, may have led to persistent infection. An alternate approach is to construct a hybrid virus using coat protein sequences from both FHV and NOV. NOV RNAs can multiply in transfected insect cells without producing cytopathic, effects (Ball et al., 1992). The polymerase encoded by RNA-1 recognizes sequences from either FHV or NOV.

For any of these approaches, an FHV-based vector having a gene of interest, or a library of genes, is introduced into host cells by infection/transfection and a change in the phenotype detected. For example, genes whose protein products lead to enhancement or suppression of a disease, changes in eye shape and color, development, growth and body weight, and the like, can thus be identified and analyzed in a short period of time.

References

Abel et al., *Science*, 232:738 (1986).
Agranovsky et al., *J. Gen. Virol.*, 79:889 (1998).
Alexander et al., *Mol. Plant-Microbe Interact*, 5:513 (1992).
Alexander et al., *Proc. Natl. Acad. Sci. USA*, 90:7327 (1993).
Alexander et al., In: *Advances in Molecular Genetics of Plant Microbe Interactions*. Kluwer Academic Publishers, Netherlands 3:527 (1993).
Allison et al., *Proc. Natl. Acad. Sci. USA*, 87:1820 (1990).
Bailey and Scott, *Nature*, 241:545 (London) (1972).
Bailey et al., *J. Gen. Virol.*, 26:15 (1975).
Balil, *J. Virol.*, 66:2335 (1992).
Barkai-Golan et al., *Arch. Microbiol.*, 116:119 (1978).
Ball et al., *J. Virol.*, 66:2326 (1992).
Barton et al., *Plant Physiol.*, 85:1103 (1987).
Beachy, *Curr. Opin. Biotechnol.*, 8:187 (1997).
Bernal-Lugo and Leopold, *Plant Physiol.*, 98:1207 (1992).
Bevan et al., *Nature*, 314:184 (1983).
Bevan et al., *Nucl. Acid Res.*, 11:369 (1983).
Blackman et al., *Plant Physiol.*, 100:225 (1992).
Bol, Linthorst, and Cornelissen, *Ann. Rev. Phytopath.*, 28:113 (1990).
Bouchez et al., *EMBO J.*, 8:4197 (1989).
Bowen, Ph.D. thesis, University of Wisconsin-Madison (1995).
Bowen et al., *Science*, 280: 2129 (1998).
Bowler et al., *Ann. Rev. Plant Physiol.*, 43:83 (1992).
Branson and Guss, *Proc. North Central Branch Ento. Soc. Am.*, 27:95 (1972).
Briggs and Helentjaris, *Genome Res.*, 7:856 (1997).
Broakaert et al., *Science*, 245:1100 (1989).
Bruening, In: *Comprehensive Virology*, H. Frankel Conrat and R. R. Wagner (Eds.), Plenum Press, New York (1977).
Brugidou et al., *Virology*, 206:108 (1995).
Callis et al, *Genes & Develop.*, 1:1183 (1987).
Campbell, W. C., Ed., *Avermectin and Abamectin* (1989).
Casper, and Holt, *Gene*, 173:69 (1996).
Chandler et al., *The Plant Cell*, 1:1175 (1989).
Chen et al., *Mol. Ecology*, 5:73 (1996).
Chia et al., *Plant Mol. Biol.*, 18:1091 (1992).
Christou et al., *Plant Physiol.*, 87:671 (1988).
Christou, *Plant Mol. Biol.*, 35:197 (1997).
Coe et al., In: *Corn and Corn Improvement*, Sprague and Dudley (eds.), pp. 81–7258 (1988).
Cooper et al., *Virology*, 216:208 (1996).
Coruzzi et al., *EMBO J.*, 3, 1671 (1984),
Coxson et al., *Biotropica*, 24:121 (1992).
Cutler et al., *J. Plant Physiol.*, 135:351 (1989).
Czapla & Lang, *J. Econ. Entomol.*, 83:2480 (1990).
Dasgupta et al., *Virology*, 104:339 (1980).
Dasgupta et al., *Nucl. Acids Res.*, 12:7215 (1984).
Dasgupta and Sgro, *Nucl. Acids Res.*, 17:7525 (1989).
Dasgupta, In: *Virology in the Tropics*, Narayan Rishi, K. L. Ahuja and B. P. Singh, (Eds.), Malhotra Publishing House, New Delhi, India (1994).
Dasgupta and Rueckert, *Arch. Virol.*, 9:121 (1994).
Dasmahapatra et al., *J. Mol. Biol.*, 182:183 (1985).
Dasmahapatra et al., *Proc. Natl. Acad. Sci. USA*, 83:63 (1986).
Davies et al., *Plant Physiol.* 93:588 (1990).
Dekeyser et al., *The Plant Cell*, 2:591 (1990).
De Jong and Ahlquist, *Proc. Natl. Acad. Sci. U.S.A.*, 89:6808 (1992).
Dellaporta et al., In: *Chromosome Structure and Function: Impact of New Concepts*, 18th Stadler Genetics Symposium, Gustafson and Appels (eds.) NY, pp. 263–282 (1988).
Deom et al., *Protoplasma*, 199:1 (1997).
Deom et al., *Proc. Natl. Acad. Sci. USA*, 87:3284 (1990).
Deom et al., *Cell*, 69:221 (1992).
Ducasse et al., *J. Virol.*, 69:5781 (1995).
Dure et al., *Plant Mol. Biol.*, 12:475 (1989).
Epel et al., *Gene*, 173:175 (1996).
Erdmann et al., *J. Gen. Microbiol.*, 138:363 (1992).
Estruch et al., *Nat. Biotechnol.*, 15:137 (1997).
Evans et al., *Trends Genet.*, 13:370 (1997).
Fisher and Johnson, *Nature*, 361:176 (London) (1993).
Fecker et al., *Plant Mol. Biol.*, 32:979 (1996).
Fitzpatrick, *Gen. Engineering News*, 22:7 (1993).
Franken et al., *Curr. Opin. Biotechnol.*, 8:411 (1997).
Frerichs et al., *J. Cen, Virol.*, 77:2067 (1996).
Friesen and Rueckert, *J. Virol.*, 37:876 (1981).
Friesen and Rueckert, *J. Virol.*, 42:986 (1982).
Gallagher et al., *J. Virol.*, 46:481 (1983).
Gallagher, T. M. Ph.D. thesis. UW-Madison (1987).
Gallie et al., The Plant Cell, 1:301 (1989).
Gan et al., *Science*, 270:1986 (1995).
Gardner et al., *Nucl. Acids Res.*, 9:2871 (1981).
Gatehouse et al., *J. Sci. Food Agric.*, 35:373 (1984).
Geske et al., *Arch. Virol.*, 141:541 (1996).
Gordon-Kamm et al., *The Plant Cell*, 2:603 (1990.).
Goring et al., *Proc. Natl. Acad. Sci. USA*, 88, 1770 (1991).
Guerrero et al., *Plant Mol. Biol.*, 15:11 (1987).
Guerrero et al., *Plant Molecular Biology*, 15:11 (1990).
Gupta et al., *Proc. Natl. Acad. Sci. USA*, 90:1629 (1993).
Hacker et al., *Virology*, 186:1 (1992).
Hammock et al., *Nature*, 344:458 (1990).
Hayashimoto et al., *Plant Physiol.*, 93, 857 (1990).
Helguera et al., *Plant Dis.*, 81: 1005 (1997).
Hemenway et al., *The EMBO J.*, 7:1273 (1988).
Hendry, In: *Viruses of Invertebrates*, pp. 227–276, E. Kurstak (Ed.), Marcel Dekker, Inc. New York, (1991).
Hinchee et al., *Bio/technol.*, 6:915 (1988).
Hilder et al., *Nature*, 330:160 (1987).
Horsch et al., *Science*, 227, 1229 (1985).
Hosur et al., *Struc. Funct. Genet.*, 2:167 (1987).
Hudspeth et al., *Plant Mol. Biol.*, 12:579 (1989).
Ikeda et al., *J. Bacteriol.*, 169:5615 (1987).
Ikuta et al., *Bio/technol.*, 8:241 (1990).
Jefferson, *Plant Mol. Bio. Rep.*, 5:387 (1987).
Jelkmann, *J. Gen. Virol.*, 75:1535 (1994).
Johnson et al., *Ann. Rev. Phytopath.*, 35:67 (1997).
Johnson et al., *Proc. Natl. Acad. Sci USA*, 86:9871 (1989).
Kaasen et al., *J. Bacteriol.*, 174:889 (1992).
Karasev et al. *FEBS Lett.*, 304:12 (1992).
Karsten et al., *Botanica Marina*, 35:11 (1992).
Katz et al., *J. Gen. Microbiol.*, 129:2703 (1983).
Kay et al., *Science*, 23:1299 (1987).
Khan and Brooks, *J. Invertebr. Path.*, 29:253 (1977).
Kaplan et al., *Virology*, 209:188 (1995).
Karsten et al., *Botanica Marina*, 35:11 (1992).
Keller et al., *The EMBO J.*, 8:1300 (1989).
Klassen et al., *J. Gen. Virol.*, 75:1525 (1994).
Kollar et al., *Biochimie*, 75:623 (1993).
Koster and Leopold, *Plant Physiol.*, 88:829 (1988).
Kraft et al., *Biotechniques*, 6:544 (1988).

Laursen et al., *Plant Mo. Biol.*, 24:51 (1994).
Lawton et al., *Plant Mol. Biol*, 9:315 (1987).
Lee and Saier, *J. Bacteriol.*, 153 (1982).
Levings, *Science*, 250:942 (1990).
Levis et al., *Proc. Natl. Acad. Sci. USA*, 84:4811 (1987).
Longworth and Archibald, *N.Z.J. Zool.* 2:233 (1975).
Loomis et al., *J. Expt. Zool.*, 252:9 (1989).
Ma and Hein, *Ann. N.Y. Acad. Sci.*, 792:72 (1996).
McCabe et al., *Bio/Tech.*, 6:923 (1988).
MacFarlane et al., *J. Gen. Virol.*, 76:1299 (1995).
Mariani et al., *Nature*, 347:737 (1990).
Matthews, In: *Plant Virology*, 3rd ed., Academic Press, pp. 262–269 (1991).
McElroy et al., *Plant Cell*, 2, 163 (1990).
McKusick, *Genomics*, 45:244 (1997).
Miele, *Trends Biotechnol.*, 15:45 (1997).
Molnar et al., *J. Gen. Virol.*, 78:1235 (1997).
Moore et al., *J. Gen. Virol.*, 66:647 (1985).
Mori et al., *Virology*, 187:368 (1992).
Mundy and Chua, *EMBO J.*, 7:2279 (1988).
Murakami et al., *Mol-Gen. Genet.*, 205:42 (1986).
Murdock et al., *Phytochem.*, 29:85 (1990).
Murry et al., *Nucl. Acids Res.*, 17:477 (1989).
Napoli et al., *Plant Cell*, 2:279 (1990).
Neelman et al., *Virology*, 181:687 (1991).
Nelson et al., *Bio/technol.*, 6:403 (1988).
Nelson et al., *Progress in Botany*, 59:476 (1998).
Newman and Brown, *J. Gen. Virol.*, 21:371 (1973).
Newman and Brown, *J. Gen. Virol.*, 38:83 (1977).
Newman et al., *J. Virol.*, 25:78 (1978).
Niedz et al., *Plant Cell Rep.*, 14, 403 (1995).
Nishizawa et al., *J. Gen. Virol.*, 76:1563 (1995).
Odell et al., *Nature*, 313:810 (1985).
Ow et al., *Scince*, 234:856 (1986).
Palmgren, *Trends Genet.*, 13:348 (1997).
Pattniak and Wertz, *Proc. Natl. Acad. Sci. USA*, 88:1379 (1991).
Perlak et al., *Proc. Natl. Acad. Sci.* 88:3324 (1991).
Phi-Van et al., *Mol. Cell Biol.*, 10:2302 (1990).
Piatkowski et al., *Plant Physiol.*, 94:1682 (1990).
Pietrzak et al., *Nucl. Acids Res.*, 14:5857 (1986).
Porta et al., *Intervirology*, 39:79 (1996).
Potrykus et al., *Mol. Gen. Genet.*, 199:83 (1985).
Potrykus, *Trends in Biotech.*, 7:269 (1989).
Prasher et al., *BBRC*, 126:1259 (1985).
Pruss et al., *Plant Cell*, 9:859 (1997).
Ravelonandro et al., *Gene*, 120:167 (1992).
Reed et al., *J. Gen. Microbiol.*, 130:1 (1984).
Reimann-Philipp and Beachy, *Mol. Plant Microbe Interact.*, 6:323 (1993).
Reinganum et al., *Intervirology*, 24:10 (1985).
Rensburg et al., *J. Plant Physiol.*, 141, 188 (1993).
Ryals et al., *Plant Cell*, 8:1809 (1996).
Sacher et al., *J. Virol.*, 63:4545 (1989).
Sambrook et al., *Molecular Claning: A Laboratory Manual*, 2ed, Cold Spring Harbor Laboratory, Cold Spring Harbor, N.Y. (1989).
Schell, *Curr. Opin. Biotechnol.*, 8:235 (1997).
Scherer and Hurlbut, *Amer. J. Epidemiol.*, 86:271 (1967).
Scherer et al., *Amer. J. Tropical Med. Hyg.*, 17:120 (1968).
Schneemann et al., *J. Virol.*, 67:2756 (1993).
Schneemann et al., *Advances in Virus Research*, 50:381 (1998).
Scorza et al., *J. Am. Soc. Hort. Sci.*, 120:943 (1995).
Scott, *Australian Plant Path*, 23:154 (1994).
Selling et al., *Proc. Natl. Acad. Sci. USA*, 87:434 (1990).
Selling and Rueckert, *J. Virol.*, 51:251 (1984).
Selling, B., Ph.D., thesis, University of Wisconsin-Madison (1986).
Sengupta-Gopalan, *Proc. Natl. Acad. Sci. USA*, 82, 3320 (1985).
Seron and Haenni, *Mol. Plant-Microbe Interact.*, 9:435 (1996).
Shagan et al., *Plant Physiol.*, 101:1397 (1993).
Shapiro, *Mobile Genetic Elements*, Academic Press, NY (1983)
Skriver and Mundy, *Plant Cell*, 2:503 (1990).
Slightom, *Gene*, 100:251 (1991).
Smith et al., *Mol. Gen. Genet.*, 224:447 (1990).
Solovyev et al., *Virology*, 217:435 (1996).
Spencer et al., *Plant Mol. Biol.*, 18:201 (1992).,
Stalker et al., *J. Biol. Chem.*, 263:6310 (1988).
Stief et al., *Nature*, 341:343 (1989).
Stiefel et al., *The Plant Cell*, 2:785 (1990).
Stouggard, *The Plant Cell*, 2:755 (1993).
Sullivan et al., *Mol. Gen. Genet.*, 215:431 (1989).
Sung et al., *J. Gen. Virol.*, 76:2809 (1995).
Sutcliffe, *Proc. Natl. Acad. Sci. USA*, 75:3737 (1978).
Tarczynski et al., *Proc. Natl. Acad. Sci. USA*, 89:2600 (1992).
Tarczynski et al., *Science*, 259:508 (1993).
Tavassa et al., *J. Gen. Virol.*, 75:1515 (1994).
Tesh, *J. Gen. Virol.*, 48:177 (1980).
Thillet et al., *J. Biol. Chem.*, 263:12500 (1988).
Torregrosa et al., *Plant Cell Tissue & Organ Culture*, 49:53 (1997).
Truve et al., *Bio/Technology*, 11:1048 (1993).
Twell et al., *Plant Physiol.*, 91:1271 (1989).
Vaeck et al., *Nature*, 328:33 (1987).
van der Krol et al., *Plant Cell*, 2:291 (1990).
van der Vossen et al., *Virology*, 212:663 (1995).
Vasil et al., *Plant Physiol.*, 91:1575 (1989).
Vernon and Bohnert, *EMBO J.*, 11:2077 (1992).
Verwoerd et al., *Nucl. Acid Res.*, 17, 2362 (1989).
Walker et al., *Proc. Natl. Acad. Sci. USA*, 84:6624 (1987).
Wang et al., *Mol. Cell. Biol.*, 12:3399 (1992).
Watrud et. al., In: *Engineered Organisms and the Environment*, Halvorsen et al. (eds.), ASM, Wash., D.C. (1995).
Weiland et al., *Virology*, 201:116 (1994).
Weising et al. *Ann. Rev. Genet.*, 22:421 (1988).
Wellink et al., *Biochimie*, 75:741 (1993).
Wery et al., *J. Mol. Biol.*, 235:565 (1994).
Wolter et al., *The EMBO J.*, 4685 (1992).
Wyn-Jones and Storey, In: *Physiology and Biochemistry of Drought Resistance in Plants*, Paleg et al. (eds.), pp. 171–204 (1981).
Xiang and Guerra, *Plant Physiol.*, 102:287 (1993).
Xiong et al., *Science*, 243:1188 (1989).
Xiong and Lommel, *Virology*, 182:388 (1991).
Xiong et al., *Virology*, 192:27 (1993).
Yamaguchi-Shinozaki et al., *Plant Cell Physiol.*, 33:217 (1992).
Yang et al., *Proc. Natl. Acad. Sci. USA*, 8:4144 (1990).
Yusibov et al., *Proc. Natl. Acad Sci. U.S.A.*, 94:5784 (1997).
Zhang et al., *Acta Botanica Sinica*, 39:236 (1997).
Zheng et al., *Theor. & Applied Genetics*, 94:522 (1997).
Zhong et al., *Proc. Natl. Acad. Sci. USA*, 89:11146 (1992).
Zhong, W. Ph. D., Thesis, UW-Madison (1993).
Zukowsky et al., *Proc. Natl. Acad. Sci. USA*, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A recombinant plant gene transfer vector comprising
(i) linked nucleic acid sequences comprising:
   (a) a nucleic acid sequence having the sequence of flock house virus RNA-1; and
   (b) a nucleic acid sequence comprising at least one nucleic acid segment of interest, wherein the nucleic acid segment of interest is not from flock house virus and comprises an open reading frame which encodes a plant virus movement protein, a plant virus coat protein, a growth hormone, a toxin, a cytokine, a gene product which confers disease resistance, a gene product which confers pest resistance, a gene product which confers male sterility, antigenic sites on the surface of a virus, a gene product which confers pesticide resistance, an antisense RNA sequence, or an antisense RNA enzyme or wherein said open reading frame comprises a synthetic gene; or (ii) linked nucleic acid sequences comprising:

(a) a nucleic acid sequence having the sequence of flock house virus RNA-2; and (b) a nucleic acid sequence comprising at least one nucleic acid segment of interest, wherein the nucleic acid segment of interest is not from flock house virus and comprises an open reading frame which encodes a plant virus movement protein, a plant virus coat protein, a growth hormone, a toxin, a cytokine, a gene product that confers disease resistance, a gene product that confers pest resistance, a gene product that confers male sterility, antigenic sites on the surface of a virus, a gene product that confers pesticide resistance, an antisense RNA sequence, or an antisense RNA enzyme or wherein said open reading frame comprises a synthetic gene;

wherein the linked sequences are expressed in a plant cell so as to yield a product of the open reading frame and can be replicated in the presence of flock house virus polymerase in the plant cell, and wherein the vector is a DNA vector or a RNA vector.

2. The vector of claim 1, wherein the linked nucleic acid sequences further comprise multiple cloning sites.

3. The vector of claim 2 wherein the nucleic acid segment encodes a plant virus movement protein.

4. The vector of claim 2 wherein the nucleic acid segment encodes a plant virus coat protein.

5. The vector of claim 2 wherein the linked nucleic acid sequences further comprise a marker gene or a selectable marker gene.

6. The vector of claim 3 or 4 wherein the linked nucleic acid sequences further comprise a marker gene or a selectable marker gene.

7. The vector of claim 3 or 5 wherein the linked nucleic acid sequences further comprise nucleic acid which encodes a plant virus coat protein.

8. The vector of claim 4 or 5 wherein the linked nucleic acid sequences further comprise nucleic acid encoding a plant virus movement protein.

9. The vector of claim 1 wherein the nucleic acid segment encodes a plant virus movement protein.

10. The vector of claim 1 wherein the nucleic acid segment encodes a plant virus coat protein.

11. The vector of claim 6 wherein the linked nucleic acid sequences encode a fusion polypeptide comprising the marker or selectable marker and the plant virus coat protein or the plant virus movement protein.

12. The vector of claim 1 wherein the linked sequences are RNA sequences.

13. The vector of claim 1 wherein the open reading frame is in an antisense orientation relative to the nucleic acid sequence of (a) of (i) or (ii).

14. The vector of claim 3 wherein the nucleic acid segment encodes tobacco mosaic virus movement protein.

15. The vector of claim 8 wherein the nucleic acid segment encodes tobacco mosaic virus movement protein.

16. The vector of claim 9 wherein the nucleic acid segment encodes tobacco mosaic virus movement protein.

17. The vector of claim 1 wherein the nucleic acid segment encodes a toxin.

18. The vector of claim 17 wherein the nucleic acid segment encodes a *Photorhabdus luminescens* toxin, Xenorhabdus toxin, Botulinum toxin or cholera toxin.

19. A nucleic acid composition, comprising:
    (a) isolated RNA-1 of flock house virus; and
    (b) a recombinant RNA comprising the vector of claim 12.

20. A nucleic acid composition, comprising:
    (a) isolated RNA-1 of flock house virus; and
    (b) a recombinant RNA molecule comprising linked RNA sequences comprising:
        RNA-1 or RNA-2 of flock house virus and RNA encoding a plant virus movement protein.

21. A nucleic acid composition, comprising:
    (a) isolated RNA-1 of flock house virus; and
    (b) a recombinant RNA molecule comprising linked RNA sequences comprising:
        RNA-1 or RNA-2 of flock house virus and RNA encoding a plant virus coat protein.

22. A method of expressing a gene product encoded by a recombinant RNA in a plant host cell, comprising:
    (a) contacting the plant host cell with an amount of the composition of claim 19, 20 or 21; and
    (b) detecting or determining whether the gene product encoded by the recombinant RNA is expressed.

23. The method of claim 22 wherein the host cell is a dicot cell.

24. The method of claim 22 wherein the host cell is a monocot cell.

25. A method comprising:
    (a) contacting a plant host cell with an amount of the composition of claim 19; and
    (b) detecting or determining whether the open reading frame in the nucleic acid segment is expressed.

26. The method of claim 25 wherein the host cell is a dicot cell.

27. The method of claim 25 wherein the host cell is a monocot cell.

28. A method of introducing a nucleic acid segment into a plant, or part thereof, comprising: contacting a plant, or part thereof, which expresses a flock house virus polymerase with an amount of the vector of claim 12 so as to yield a plant, or part thereof, having cells which express said open reading frame.

29. The method of claim 28 wherein the nucleic acid segment encodes a growth hormone, a toxin, a cytokine, a gene product that confers disease resistance, a gene product that confers pest resistance, a gene product that confers male sterility, or a gene product that confers pesticide resistance.

30. The method of claim 28 wherein the plant is contacted by spraying or rubbing.

31. A method of introducing a recombinant RNA into a plant, comprising: contacting a plant with an amount of the composition of claim 19, 20 or 21 so as to yield a plant having cells which comprise the recombinant RNA.

32. The method of claim 31 wherein the recombinant RNA molecule further encodes a growth hormone, a toxin, a cytokine, a gene product that confers disease resistance, a gene product that confers pest resistance, a gene product that confers male sterility, or a gene product that confers pesticide resistance.

33. The method of claim 31 wherein the plant is contacted by spraying or rubbing.

34. A recombinant flock house virus, comprising:
    a first flock house virus RNA molecule which is capable of replication in a plant cell in the presence of flock house virus polymerase; and
    a second recombinant RNA molecule comprising RNA-1 or RNA-2 of flock house virus and a sequence which encodes a plant virus coat protein, a plant virus movement protein, or a combination thereof.

35. A transgenic plant, or part thereof, comprising the vector of claim 12 and RNA-1 of flock house virus, wherein the genome of the transgenic plant, or part thereof, comprises a recombinant DNA encoding a plant virus movement protein.

36. The plant part from the plant of claim 35 wherein the plant part contains the vector.

37. The plant part of claim 36 wherein the plant part is a seed.

38. A plant produced by the method of claim 28.

39. A plant part from the plant of claim 38 wherein the plant part expresses flock house virus polymerase and contains the vector.

40. A plant part produced by the method of claim 28, wherein said plant part is a seed, wherein the seed expresses flock house virus polymerase and contains the vector.

41. A plant produced by the method of claim 29.

42. A plant part from the plant of claim 41 wherein the plant part expresses flock house virus polymerase and contains the vector.

43. A plant part produced by the method of claim 29, wherein said plant part is a seed, wherein the seed expresses flock house virus polymerase and contains the vector.

44. The vector of claim 3 wherein the nucleic acid segment encodes red clover necrotic mosaic virus movement protein.

45. The vector of claim 8 wherein the nucleic acid segment encodes red clover necrotic mosaic virus coat protein.

46. The vector of claim 9 wherein the nucleic acid segment encodes red clover necrotic mosaic virus coat protein.

47. A transgenic plant comprising the composition of claim 19, wherein the genome of the transgenic plant comprises a recombinant DNA encoding tobacco mosaic virus movement protein.

48. A transgenic plant comprising the composition of claim 19, wherein the genome of the transgenic plant comprises a recombinant DNA encoding red clover necrotic mosaic virus movement protein.

49. The transgenic plant of claim 47 or 48 which is *Nicotiana benthamiana*.

* * * * *

UNITED STATES PATENT AND TRADEMARK OFFICE
CERTIFICATE OF CORRECTION

PATENT NO. : 6,700,038 B1
DATED : March 2, 2004
INVENTOR(S) : Dasgupta et al.

It is certified that error appears in the above-identified patent and that said Letters Patent is hereby corrected as shown below:

Title page,
Item [56], References Cited, OTHER PUBLICATIONS, "Solovyev et al," after "1997." insert -- * --.
"Zhong et al," after "1992." insert -- * --.
"Selling et al," after "1990." insert -- * --.
"Johnson, K.L., et al.," delete "Rna" and insert -- RNA --, therefor.
"Johnson, K.N., et al.," delete "large" and insert -- larger --, therefor.

Signed and Sealed this

Sixth Day of July, 2004

JON W. DUDAS
*Acting Director of the United States Patent and Trademark Office*